United States Patent

Ognyanov et al.

[11] Patent Number: 6,001,854
[45] Date of Patent: Dec. 14, 1999

[54] PHARMACEUTICAL FOR TREATING OF NEUROLOGICAL AND NEUROPSYCHIATRIC DISORDERS

[75] Inventors: Vassil Iliya Ognyanov, Franklin Park; Laurence A. Borden, Hackensack, both of N.J.; Stanley Charles Bell, Narberth, Pa.; Jing Zhang, East Brunswick, N.J.

[73] Assignee: Allelix Neuroscience Inc., Cranbury, N.J.

[21] Appl. No.: 08/865,919

[22] Filed: May 30, 1997

Related U.S. Application Data

[60] Provisional application No. 60/064,849, May 31, 1996, and provisional application No. 60/044,388, Feb. 27, 1997.

[51] Int. Cl.⁶ .................. A61K 31/445; C07D 211/06
[52] U.S. Cl. .................. 514/317; 546/239; 546/333; 546/342; 546/221
[58] Field of Search .................. 546/216, 221, 546/229, 233, 234, 239, 333, 342; 514/317, 327, 331, 357

[56] References Cited

U.S. PATENT DOCUMENTS

| | | | |
|---|---|---|---|
| 5,057,524 | 10/1991 | Walsh | 514/317 |
| 5,153,207 | 10/1992 | Ito et al. | 514/327 |
| 5,837,730 | 11/1998 | Javitt | 514/551 |

OTHER PUBLICATIONS

Takahara, E. et al.: Analysis of urinary and biliary metabolites of (+) –MMPB in rats by liquid chromatography–frit–fast atom bombardment mass spectrometry. J. of Chromatography, vol. 658, pp. 154–160, 1994.

Edited by Bennett, J. Claude; Plum, Fred, *Cecil Textbook of Medicine*, Vol. 2: 1992–1994 (1996).

Danysz, W. and Parsons, C., *Pharmacol. Rev.*, Vol. 50(4), 597 (1998).

*Primary Examiner*—John Kight
*Assistant Examiner*—Charanjit S. Aulakh
*Attorney, Agent, or Firm*—Dechert Price & Rhoads

[57] ABSTRACT

The invention provides a pharmaceutical for treatment of neurological and neuropsychiatric disorders comprising a compound of the following formulas I and II:

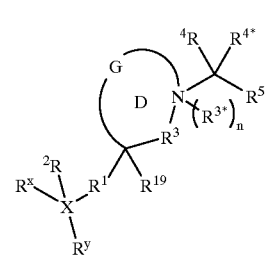

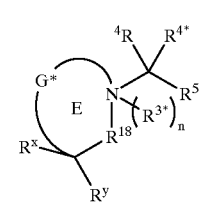

or a pharmaceutically acceptable salt thereof.

25 Claims, 1 Drawing Sheet

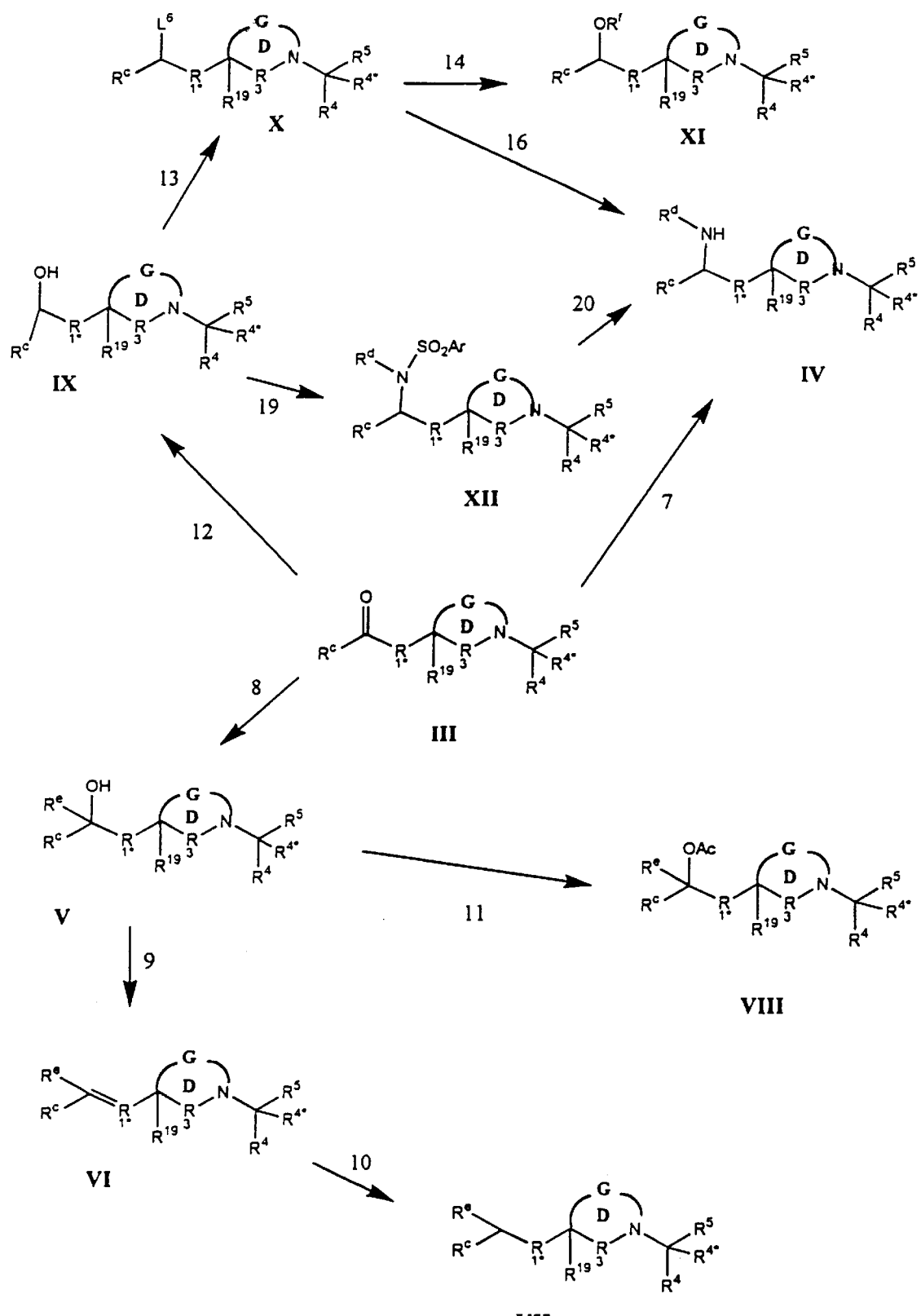
FIG.

PHARMACEUTICAL FOR TREATING OF NEUROLOGICAL AND NEUROPSYCHIATRIC DISORDERS

The present application is a continuation-in-part of U.S. Ser. No. 08/655,847, filed May 31, 1996, now converted to a provisional application U.S. Ser. No. 60/064,849, and a continuation-in-part of U.S. Ser. No. 08/807,681, filed Feb. 27, 1997, now converted to a provisional application U.S. Ser. No. 60/044,388.

The present invention relates to a class of substituted cyclic amines, pharmaceutical compositions and methods of treating neurological and neuropsychiatric disorders.

Synaptic transmission is a complex form of intercellular communication that involves a considerable array of specialized structures in both the pre- and post-synaptic neuron. High-affinity neurotransmitter transporters are one such component, located on the pre-synaptic terminal and surrounding glial cells (Kanner and Schuldiner, CRC Critical Reviews in Biochemistry, 22, 1032 (1987)). Transporters sequester neurotransmitter from the synapse, thereby regulating the concentration of neurotransmitter in the synapse, as well as its duration therein, which together influence the magnitude of synaptic transmission. Further, by preventing the spread of transmitter to neighboring synapses, transporters maintain the fidelity of synaptic transmission. Last, by sequestering released transmitter into the presynaptic terminal, transporters allow for transmitter reutilization.

Neurotransmitter transport is dependent on extracellular sodium and the voltage difference across the membrane; under conditions of intense neuronal firing, as, for example, during a seizure, transporters can function in reverse, releasing neurotransmitter in a calcium-independent non-exocytotic manner (Attwell et al., Neuron, 11, 401–407 (1993)). Pharmacologic modulation of neurotransmitter transporters thus provides a means for modifying synaptic activity, which provides useful therapy for the treatment of neurological and psychiatric disturbances.

The amino acid glycine is a major neurotransmitter in the mammalian central nervous system, functioning at both inhibitory and excitatory synapses. By nervous system, both the central and peripheral portions of the nervous system are intended. These distinct functions of glycine are mediated by two different types of receptor, each of which is associated with a different class of glycine transporter. The inhibitory actions of glycine are mediated by glycine receptors that are sensitive to the convulsant alkaloid strychnine, and are thus referred to as "strychnine-sensitive." Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine functions in excitatory transmission by modulating the actions of glutamate, the major excitatory neurotransmitter in the central nervous system. See Johnson and Ascher, Nature, 325, 529–531 (1987); Fletcher et al., Glycine Transmission, (Otterson and Storm-Mathisen, eds., 1990), pp. 193–219. Specifically, glycine is an obligatory co-agonist at the class of glutamate receptor termed N-methyl-D-aspartate (NMDA) receptor. Activation of NMDA receptors increases sodium and calcium conductance, which depolarizes the neuron, thereby increasing the likelihood that it will fire an action potential. NMDA receptors are widely distributed throughout the brain, with a particularly high density in the cerebral cortex and hippocampal formation.

Molecular cloning has revealed the existence in mammalian brains of two classes of glycine transporters, termed GlyT-1 and GlyT-2. GlyT-1 is found predominantly in the forebrain, and its distribution corresponds to that of glutamatergic pathways and NMDA receptors (Smith, et al., Neuron, 8, 927–935 (1992)). Molecular cloning has further revealed the existence of three variants of GlyT-1, termed GlyT-1a, GlyT-1b and GlyT-1c (Kim, et al., Molecular Pharmacology, 45, 608–617 (1994)), each of which displays a unique distribution in the brain and peripheral tissues. These variants arise by differential splicing and exon usage, and differ in their N-terminal regions. GlyT-2, in contrast, is found predominantly in the brain stem and spinal cord, and its distribution corresponds closely to that of strychnine-sensitive glycine receptors (Liu et al., J. Biological Chemistry, 268, 22802–22808 (1993); Jursky and Nelson, J. Neurochemistry, 64, 1026–1033 (1995)). These data are consistent with the view that, by regulating the synaptic levels of glycine, GlyT-1 and GlyT-2 selectively influence the activity of NMDA receptors and strychnine-sensitive glycine receptors, respectively.

Compounds that inhibit or activate glycine transporters would thus be expected to alter receptor function, and provide therapeutic benefits in a variety of disease states. For example, inhibition of GlyT-2 can be used to diminish the activity of neurons having strychnine-sensitive glycine receptors via increasing synaptic levels of glycine, thus diminishing the transmission of pain-related (i.e., nociceptive) information in the spinal cord, which has been shown to be mediated by these receptors. Yaksh, Pain 37, 111–123 (1989). Additionally, enhancing inhibitory glycinergic transmission through strychnine-sensitive glycine receptors in the spinal cord can be used to decrease muscle hyperactivity, which is useful in treating diseases or conditions associated with increased muscle contraction, such as spasticity, myoclonus, and epilepsy (Truong et al., Movement Disorders, 3, 77–87 (1988); Becker, FASEB J., 4, 2767–2774 (1990)). Spasticity that can be treated via modulation of glycine receptors is associated with epilepsy, stroke, head trauma, multiple sclerosis, spinal cord injury, dystonia, and other conditions of illness and injury of the nervous system.

NMDA receptors are critically involved in memory and learning (Rison and Stanton, Neurosci. Biobehav. Rev., 19, 533–552 (1995); Danysz et al., Behavioral Pharmacol., 6, 455–474 (1995)); and, furthermore, decreased function of NMDA-mediated neurotransmission appears to underlie, or contribute to, the symptoms of schizophrenia (Olney and Farber, Archives General Psychiatry, 52, 998–1007 (1996). Thus, agents that inhibit GlyT-1 and thereby increase glycine activation of NMDA receptors can be used as novel antipsychotics and anti-dementia agents, and to treat other diseases in which cognitive processes are impaired, such as attention deficit disorders and organic brain syndromes. Conversely, over-activation of NMDA receptors has been implicated in a number of disease states, in particular the neuronal death associated with stroke and possibly neurodegenerative diseases, such as Alzheimer's disease, multi-infarct dementia, AIDS dementia, Huntington's disease, Parkinson's disease, amyotrophic lateral sclerosis or other conditions in which neuronal cell death occurs, such as stroke or head trauma. Coyle & Puttfarcken, Science, 262, 689–695 (1993); Lipton and Rosenberg, New Engl. J. of Medicine, 330, 613–622 (1993); Choi, Neuron, 1, 623–634 (1988). Thus, pharmacological agents that increase the activity of GlyT-1 will result in decreased glycine-activation of NMDA receptors, which activity can be used to treat these and related disease states. Similarly, drugs that directly block the glycine site on the NMDA receptors can be used to treat these and related disease states.

SUMMARY OF THE INVENTION

By the present invention, a class of compounds has been identified that inhibit glycine transport via the GlyT-1 or GlyT-2 transporters, are precursors, such as pro-drugs, to compounds that inhibit such transport, or are synthetic intermediates for preparing compounds that inhibit such transport. Thus, the invention provides a class of compounds formulas:

The present invention provides compound of one of the following formulas I and II:

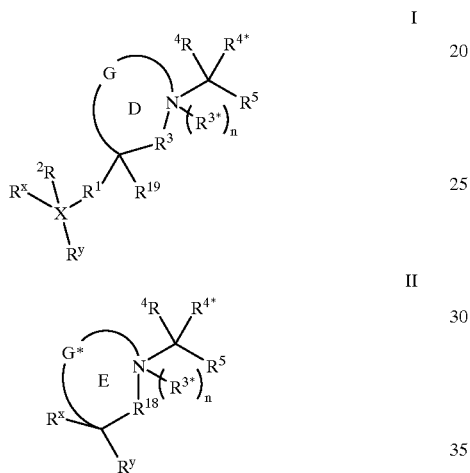

or a pharmaceutically acceptable salt thereof, wherein:

(1) X is nitrogen or carbon, and $R^2$ is not present when X is nitrogen;

(2) $R^2$ (a) is hydrogen, (C1–C6) alkyl, (C1–C6) alkoxy, cyano, (C2–C7) alkanoyl, aminocarbonyl, (C1–C6) alkylaminocarbonyl or dialkylaminocarbonyl wherein each alkyl is independently C1 to C6, (b) comprises (where $R^1$ is not —O—$R^8$or —S—$R^{8*}$) hydroxy, fluoro, chloro, bromo or (C2–C7) alkanoyloxy, (c) forms a double bond with an adjacent carbon or nitrogen from one of either $R^1$, $R^{xb}$ or $R^{yb}$, (d) is oxygen forming an oxa linkage with $R^1$ or integrated into ring E (see, for example, Compound C6) or (e) is $R^{2a}$ linked by $R^{2b}$ to X;

($2^i$) $R^x$ is a ring-containing structure $R^{xa}$ linked by $R^{xb}$ to X;

($2^{ii}$) $R^y$ is a ring-containing structure $R^{ya}$ linked by $R^{yb}$ to X;

($2^{iii}$) $R^{xa}$, $R^{ya}$ and $R^{2a}$, are independently aryl, heteroaryl, adamantyl or a 5 to 7-membered non-aromatic ring having from 0 to 2 heteroatoms selected from the group consisting of oxygen, sulfur and nitrogen, wherein:

(a) aryl is phenyl or naphthyl, (b) heteroaryl comprises a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon, (c) each of $R^{xa}$, $R^{ya}$ and $R^{2a}$ can be independently substituted with one of $R^q$, $R^rO$— or $R^sS$—, wherein Rq, Rr and Rs are independently aryl, heteroaryl, adamantyl or a 5 to 7-membered non-aromatic ring as these structures are defined for $R^{xa}$, and (d) $R^{xa}$, $R^{ya}$, $R^{2a}$, $R^q$, $R^r$ and $R^s$ can be additionally substituted with substituents selected from the group consisting of fluoro, chloro, bromo, nitro, hydroxy, cyano, trifluoromethyl, amidosulfonyl which can have up to two independent (C1–C6) N-alkyl substitutions, adamantyl, (C1–C12) alkyl [preferably (C1–C6) or (C1–C8), (C1–C12) alkenyl [preferably (C1–C6) or (C1–C8)], amino, (C1–C6) alkylamino, dialkylamino wherein each alkyl is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two independent (C1–C6) alkyl, (C1–C6) alkylsulfonyl, amidino that can independently substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl, wherein:

(i.) the substitutions of $R^{xa}$, $R^{ya}$ and $R^{2a}$ can be combined to form a second bridge between two of $R^{xa}$, $R^{ya}$ and $R^{2a}$ comprising (1) (C1–C2) alkyl or alkenyl, which can be independently substituted with one or more (C1–C6) alkyl, (2) sulfur, (3) oxygen, (4) amino, which can be substituted for hydrogen with one (C1–C6) alkyl, (5) carbonyl, (6) —CH$_2$C(=O)—, which can be substituted for hydrogen with up to two independent (C1–C6) alkyl, (7) —C(=O)—O—, (8) —CH$_2$—O—, which can be substituted for hydrogen with up to two independent (C1–C6) alkyl, (9) —C(=O)—N($R^{24}$)—, wherein $R^{24}$ is hydrogen or (C1–C6) alkyl, (10) —CH$_2$—NH—, which can be substituted for hydrogen with up to three (C1–C6) alkyl, or (11) —CH=N—, which can be substituted for hydrogen with (C1–C6) alkyl, or wherein two of $R^{xa}$, $R_{ya}$ and $R^{2a}$ can be directly linked by a single bond;

($2^{iv}$) $R^{xb}$ and $R^{2b}$ are independently a single bond or (C1–C2) alkylene;

($2^v$) $R^{yb}$ is a single bond, oxa [i.e., —O—], (C1–C2) alkylene, ethenylene or —CH= (where the double bond is with X), thia [i.e., —S—], methyleneoxy or methylenethio, or either —N($R^6$)— or —CH$_2$—N ($R^{6*}$)—, wherein $R^6$ and $R^{6*}$ are hydrogen or (C1–C6) alkyl, wherein when X is nitrogen X is not bonded to another heteroatom;

(3) $R^1$ comprises: a single bond or double bond; a straight-chained (C1–C3) aliphatic group; or (where X is carbon and $R^{yb}$ does not include a heteroatom attached to X) —O—$R^8$ or —S—$R^{8*}$, wherein either $R^8$ or $R^{8*}$ is a single bond, (C1–C3) alkylene or (C2–C3) alkenylene and O or S is bonded to X:

wherein $R^1$ can be substituted with up to one hydroxy, up to one (C1–C6) alkoxy or up to one (C2–C7) alkanoyloxy, with up to two independent (C1–C6) alkyl, with up to one oxo, up to one (C1–C6) alkylidene, with the proviso that the hydroxy, alkoxy, alkanoyloxy, oxo substituents are not bonded to a carbon that is bonded to a nitrogen or oxygen, or (where $R^1$ is —O—$R^8$ and X is carbon) an oxa linkage to X forming a 1,3-dioxolane, wherein the alkyl or alkylidene substituents of $R^1$ can be linked to form a 3 to 7-membered non-aromatic ring, and wherein if X is nitrogen, X is linked to $R^1$ by a single bond and the terminal carbon of $R^1$ that links $R^1$ to N is saturated;

(4) n is 0 or 1, and where if n is 1, $R^{3*}$ is either (C1–C6) alkyl (with the attached nitrogen having a positive charge) or oxygen (forming an N-oxide) and X is carbon;

(5) wherein ring D is a 3 to 8-membered ring, a 3 to 8-membered ring substituted with a 3 to 6-membered spiro ring, or a 3 to 8-membered ring fused with a 5 to 6-membered ring, wherein the fused ring lacking the illustrated tertiary nitrogen can be aromatic or heteroaromatic, wherein for each component ring of ring D there are up to two heteroatoms selected from oxygen, sulfur or nitrogen, including the illustrated nitrogen, and the rest carbon, with the proviso that the ring atoms include no quaternary nitrogens, with the proviso that, in saturated rings, ring nitrogen atoms are separated from other ring heteroatoms by at least two intervening carbon atoms:

wherein the carbon and nitrogen ring atoms of ring D can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C1–C6) alkoxy, oxo, hydroxycarbonyl, aryl wherein the aryl is as defined for $R^a$ or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms [where $R^3$ is preferably a single bond or (C1–C2) alkyl or alkenyl]; and wherein $R^1$, $R^3$ and G are such that at least two atoms separate X and the illustrated ring nitrogen;

(6) wherein ring E is a 3 to 8-membered ring, a 3 to 8-membered ring substituted with a 3 to 6-membered spiro ring, or a 3 to 8-membered ring fused with a 5 to 6-membered ring, wherein the fused ring lacking the illustrated tertiary nitrogen can be aromatic or heteroaromatic, wherein for each component ring of ring E there are up to two heteroatoms selected from oxygen, sulfur or nitrogen, including the illustrated nitrogen, and the rest carbon, with the proviso that the ring atoms include no quaternary nitrogens, with the proviso that, in saturated rings, ring nitrogen atoms are separated from other ring heteroatoms by at least two intervening carbon atoms:

wherein the carbon and nitrogen ring atoms of ring E can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C–C6) alkoxy, oxo [i.e., oxygen of carbonyl], hydroxycarbonyl, (C1–C6) alkoxycarbonyl, aryl wherein the aryl is as defined for $R^a$ or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms [where preferably $R^{18}$ is a single bond or ($C_1$–C3) alkyl or alkenyl]; and wherein G* and $R^{18}$ are such that at least two atoms separate the illustrated ring nitrogen from the carbon linked to $R^x$ and $R^y$;

(7) $R^{19}$ (a) forms a double bond with $R^1$, $R^3$ or G, (b) is hydrogen (c) is (C1–C3) alkyl or alkylene, or (d) is incorporated into a fused ring;

(8) $R^4$ and $R^{4*}$ are independently hydrogen or (C1–C6) alkyl, or one of $R^4$ and $R^{4*}$ can be (C1–C6) hydroxyalkyl; and (9) R5 is $(CO)NR^{13}R^{14}$, $(CO)OR^{15}$, $(CO)SR^{16}$, $(SO_2)NR^{17}R^{18}$, $(PO)(OR^{19})(OR^{20})$, $(CR^{22})(OR^{23})(OR^{24})$, CN or tetrazol-5yl, wherein $R^{13}$, $R^{14}$, $R^{15}$, $R^{16}$, $R^{17}$, $R^{18}$, $R^{19}$ and $R^{20}$ are independently hydrogen, (C1–C8) alkyl which can include a (C3–C8) cycloalkyl, wherein the carbon linked to the oxygen of R15 or the sulfur of R16 has no more than secondary branching and, (C2–C6) hydroxyalkyl, aminoalkyl where the alkyl is C2 to C6 and the amino can be substituted with up to two independent (C1–C6) alkyls, arylalkyl wherein the alkyl is C1–C6, heteroarylalkyl wherein the alkyl is C1 to C6, aryl or heteroaryl, $R^{22}$ is hydrogen or $OR^{25}$ and $R^{23}$, $R^{24}$ and $R^{25}$ are (C1–C6) alkyl, phenyl, benzyl, acetyl or, where $R^{22}$ is hydrogen, the alkyls of $R^{23}$ and $R^{24}$ can be combined to include 1,3-dioxylane or 1,3-dioxane:

wherein the aryl is phenyl or naphthyl and the heteroaryl is a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon;

wherein the aryl, heteroaryl, aryl of arylalkyl or the heteroaryl of heteroarylalkyl can be substituted with [preferably up to three] substituents selected from the group consisting of fluoro, chloro, bromo, nitro, cyano, trifluoromethyl, amidosulfonyl which can have up to two independent (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two independent (C1–C6) alkyl, (C1–C6) alkylsulfonyl, amidino that can substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl; and wherein $R^{13}$ and $R^{14}$ together with the nitrogen can form a 5 to 7-membered ring that can contain one additional heteroatom selected from oxygen and sulfur.

In a preferred embodiment, (A) at least one of $R^{xa}$, $R^{ya}$ and $R^{2a}$ is substituted with fluoro, chloro, bromo, hydroxy, trifluoromethyl, trifluoromethoxy, nitro, cyano, (C3–C8) alkyl, $R^q$, $R^rO$—, $R^sS$—, or (B) the ring structures of $R^{xa}$, $R^{ya}$ and $R^{2a}$, including substituents thereto, otherwise include at least two aromatic ring structures that together include from 15 to 20 ring atoms. Preferably, at least one of $R^{xa}$, $R^{ya}$ and $R^{2a}$ is substituted with fluoro, trifluoromethyl, trifluoromethoxy, nitro, cyano, or (C3–C8) alkyl. Preferably, at least one of $R^{xa}$, $R^{ya}$ and $R^{2a}$ is substituted with $R^q$, $R^rO$—, or $R^sS$—. Preferably, an aryl or heteroaryl of at least one of $R^{xa}$, $R^{ya}$ and $R^{2a}$ is phenyl. Preferably, $R^{yb}$ is oxa, methyleneoxy, thia, methylenethia. Preferably, $R^{yb}$ is oxa or thia. Preferably, $R^5$ is $(CO)NR^{13}R^{14}$, $(CO)OR^{15}$ or $(CO)SR^{16}$. Preferably, $R^{15}$ is (C2–C6) alkyl, (C2–C4) hydroxyalkyl, phenyl, phenylalkyl wherein the alkyl is C1–C3, or aminoalkyl where the alkyl is C2–C6 and the amino can be substituted with up to two independent (C1–C3) alkyls, wherein the phenyl or the phenyl of phenylalkyl can be substituted. Preferably, n is zero. Preferably, $R^{15}$ is hydrogen. Preferably, $R^4$ is hydrogen, methyl or hydroxymethyl and $R^{4*}$ is hydrogen. Preferably, at least one of $R^{xa}$, $R^{ya}$ and $R^{2a}$ is a heteroaryl comprising diazolyl, triazolyl, tetrazolyl, thiazolyl, isothiazolyl, oxazolyl, isoxazolyl, thiolyl, diazinyl, triazinyl, benzoazolyl, benzodiazolyl, benzothiazolyl, benzoxazolyl, benzoxolyl, benzothiolyl, quinolyl, isoquinolyl, benzodiazinyl, benzotriazinyl, pyridyl, thienyl, furanyl, pyrrolyl, indolyl, isoindoyl or pyrimidyl. Preferably, $R^1$ is —O—$R^8$ or —S—$R^{8*}$.

Preferably, the second bridge between two of $R^{xa}$, $R^{ya}$ and $R^{2a}$ is L, and satisfies the following formula:

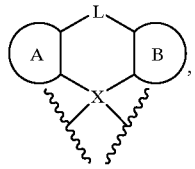

wherein A and B are aryl or heteroaryl groups of $R^{xa}$ and $R^{ya}$, respectively. Preferably, $R^{xa}$—$R^{xb}$—, $R^{ya}$—$R^{yb}$— and X form:

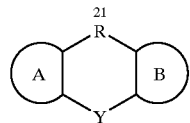

wherein Y is a carbon bonded to $R^1$ by a single or double bond or a nitrogen that is bonded to $R^1$ and wherein $R^{21}$ either (i.) completes a single bond linking two aryl or heteroaryl rings of $R^x$ and $R^y$, (ii.) is (C1–C2) alkylene or alkenylene, (iii.) is sulfur or (iv.) is oxygen, and wherein $R^x$ and $R^y$ can be substituted as set forth above. Preferably, $R^{21}$ is $CH_2CH_2$ or CH=CH. Preferably, the alkylenedioxy substitution of $R^{xa}$, $R^{ya}$ or $R^{2a}$ is as follows:

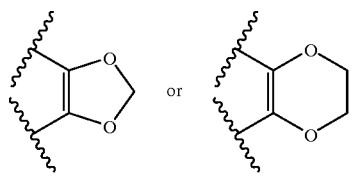

wherein the alkylenedioxy can be substituted with up to two independent (C1–C3) alkyl.

Preferably, ring D is according to one of formulas A' and B':

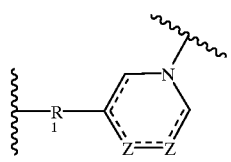

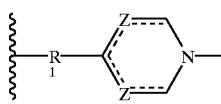

wherein Z represents carbon or nitrogen, wherein for each of formulas A' and B' up to two of the bonds indicated with the hashed lines can be double bonds provided no two double bonds are adjacent, and wherein the ring of formulas A' and B' can be substituted as set forth above for ring D. Preferably, the ring system comprising G* is according to one of formulas C' and D'

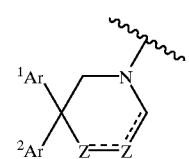

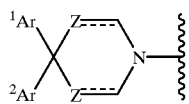

wherein Z represents carbon or nitrogen, wherein for formula C' up to one of the bonds Indicated with the hashed lines can be double bond and for formula D' up to two of the bonds indicated with the hashed lines can be double bonds, and wherein the ring can be substituted as set forth above for ring E. Preferably, ring D or ring E is substituted with up to three substituents. Preferably, $R^{xa}$ and $R^{ya}$ together can be substituted with up to six substituents, $R^{2a}$, $R^q$, $R^r$ and $R^s$ can each be substituted with up to 3 substituents, and wherein the presence of each of $R^q$, $R^r$ or $R^s$ is considered a substitution to the respective ring structure of $R^{xa}$, $R^{ya}$ and $R^{2a}$. Preferably, the aryl, heteroaryl, aryl of arylalkyl or the heteroaryl of heteroarylalkyl of $R^{13}$, $R^{14}$, $R^{15}$, $R^{16}$ $R^{17}$, $R^{18}$ $R^{19}$ or $R^{20}$ is substituted with up to three substituents. Preferably, the compound is an optically pure enantiomer. Preferably, the compound is an optically pure enantiomer (i.e., at least about 80% ee, preferably at least about 90% ee, more preferably at least about 95% ee).

Preferably, the invention provides a pharmaceutical composition comprising the compound and a pharmaceutically acceptable excipient. Preferably, the compound of the invention is present in an effective amount for: (1) treating or preventing schizophrenia, (2) enhancing treating or preventing dementia, (3) treating or preventing epilepsy, (4) treating or preventing spasticity, (5) treating or preventing muscle spasm, (6) treating or preventing pain, (7) preventing neural cell death after stroke, (8) preventing neural cell death in an animal suffering from a neurodegenerative disease, (9) treating or preventing mood disorders such as depression, (10) enhancing memory or learning, or (11) treating or preventing learning disorders. The invention further provides a method (1) of treating or preventing schizophrenia comprising administering a schizophrenia treating or preventing effective amount of a compound, (2) of treating or preventing dementia comprising administering a dementia treating or preventing effective amount of a compound, (3) of treating or preventing epilepsy comprising administering an epilepsy treating or preventing effective amount of a compound, (4) of treating or preventing spasticity comprising administering a spasticity treating or preventing effective amount of a compound, (5) of treating or preventing muscle spasm comprising administering a muscle spasm treating or preventing effective amount of a compound, (6) of treating or preventing pain comprising administering a pain treating or preventing effective amount of a compound, (7) of preventing neural cell death after stroke comprising administering a neural cell death preventing effective amount of a compound, (8) of preventing neural cell death in an animal suffering from a neurodegenerative disease, (9) treating or preventing mood disorders such as depression, (10) enhancing memory or learning, or (11) treating or preventing learning disorders, comprising administering an amount effective for said treating, preventing or enhancing of the compound. Preferably, the spasticity treated or prevented is associated with epilepsy, stroke, head trauma, multiple sclerosis, spinal cord injury or dystonia. Preferably, the neurodegenerative disease treated or prevented is Alzheimer's disease, multi-infarct dementia, AIDS dementia, Parkinson's disease, Huntington's disease, amyotrophic lateral sclerosis or stroke or head trauma such as results in neuronal cell death.

The invention also provides a method of synthesizing a compound of the invention comprising:

A) reacting a compound of the formula

1)

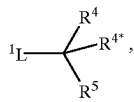

wherein $^1L$ is a nucleophilic substitution leaving group, with a compound of the formula

2)

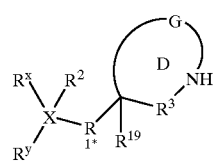

or

B) reacting a compound of the formula

1)

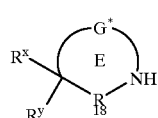

with a compound of the formula

2)

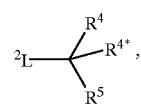

wherein $^2L$ is a nucleophilic substitution leaving group.

The invention also provides a method of synthesizing a compound of the invention comprising reductively alkylating $R^dNH_2$ with a compound of the formula

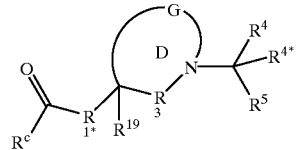

wherein $R^c$ and $R^d$ are independently the same as defined for $R^x$, and wherein $R^{1*}$ has the same definition as $R^1$ except that it does not include a nitrogen, oxygen or sulfur, and does not include any double bonds conjugated with the above-illustrated carbonyl.

The invention also provides a method of synthesizing a compound of the invention comprising reacting $R^fOH$ or $R^{f*}SH$ with a compound of the formula

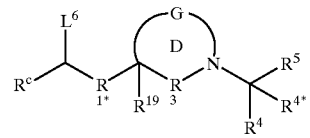

to form an ether or a thioether, respectively, wherein $R^f$ and $R^{f*}$ are independently the same as defined for $R^x$, and wherein $R^{1*}$ has the same definition as $R^1$ except that it does not include a nitrogen, oxygen or sulfur, and does not include any double bonds at the atom bonded to the above-illustrated $L^6$-substituted carbon. Preferably, the method further comprises synthesizing the compound of formula

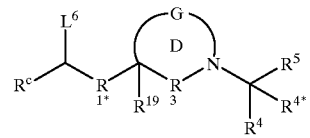

by replacing the hydroxyl of formula

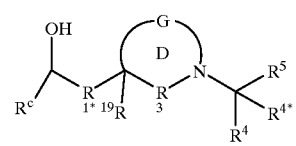

with another nucleophilic substitution leaving group. Preferably, the method comprises reacting a compound of formula

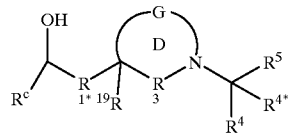

with an azodicarboxylate in the presence of a phosphine compound.

The invention also provides a method of synthesizing a compound of the invention comprising reacting $R^eM$ with a compound of the formula

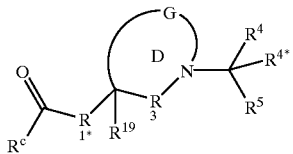

to form a compound of the formula

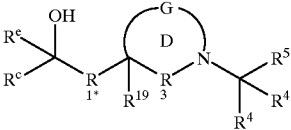

wherein $R^e$ is independently the same as defined for $R^x$, wherein M is a metal-containing substituent such that $R^eM$ is a organometallic reagent.

The invention also provides a method of synthesizing a compound of the invention comprising dehydrating a compound of the formula

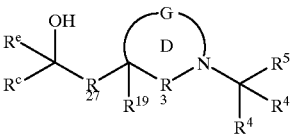

to form a compound of the formula

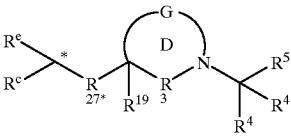

wherein C* (the tertiary carbon marked with an adjacent "*") has a double bond with an adjacent carbon, wherein $R^{27}$ and $R^{27*}$ have the same definition as $R^1$ except that $R^{27}$ and $R^{27*}$ do not include a nitrogen, oxygen or sulfur.

The invention also provides a method of synthesizing a compound of the invention comprising reducing a compound of the formula

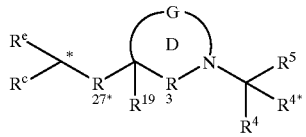

wherein C* has a double bond with an adjacent carbon, to form a compound of the formula

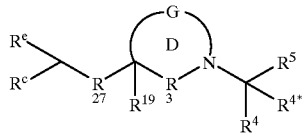

The invention also provides a method of synthesizing a compound of the invention comprising reducing a compound of one of the following formulas

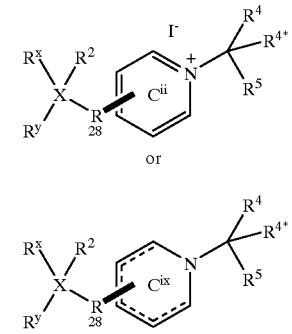

to reduce a double bond in ring $C^{ii}$ or ring $C^{ix}$, wherein $R^{28}$ is the same as $R^1$ except that the bond to the ring is not a double bond, wherein ring $C^{ix}$ is mono or di-unsaturated at one or more of the bonds indicated with the dased lines with the double bonds formed between ring carbons and no two double bonds are adjacent, wherein ring $C^{ii}$ or ring $C^{ix}$ can include a fused phenyl and can be substituted as follows the carbon and nitrogen ring atoms of ring $C^{ii}$ or ring $C^{ix}$ can be substituted with up to two substituents selected from (C1–C6) alkyl, (C2–C6) alkenylene, cyano, nitro, trifluoromethyl, and (C2–C7) alkyloxycarbonyl, and wherein $I^-$ is a negative counter-ion.

Preferably, the compound reduced is that containing ring $C^{ii}$.

The invention also provides a compound according to the following formula

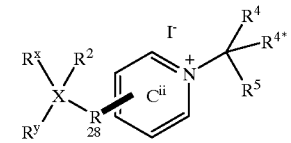

that can be used to synthesize a compound of the invention. The invention also provides a method of synthesizing this compound comprising reacting a compound of the formula

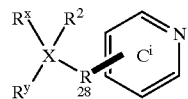

with a compound of the formula

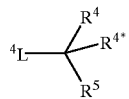

wherein $L^4$ is a nucleophilic substitution leaving group and wherein ring $C^i$ can be fused with phenyl or substituted, the same as defined for ring $C^{ii}$.

The invention also provides a compound of the invention according to the following formula

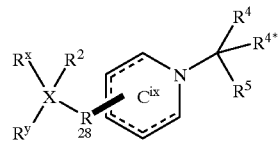

wherein ring $C^{ix}$ can be fused with phenyl or substituted, the same as defined for ring $C^{ii}$, and is mono or di-unsaturated at one or more of the bonds indicated with the dased lines with the double bonds formed between ring carbons and no two double bonds are adjacent The invention also provides a compound of the following formula

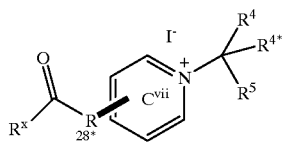

that can be used to synthesize a compound of the invention, wherein $I^-$ is a negative counter-ion, wherein $R^{28*}$ is a (C1–C3) aliphatic group that can be substituted as defined for $R^1$, wherein ring $C^{vii}$ can be fused with phenyl or substituted, the same as defined for ring $C^{ii}$. The invention also provides a method of synthesizing this compound comprising reacting a compound of the formula

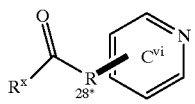

with a compound of the formula

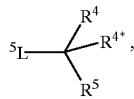

wherein $L^5$ is a nucleophilic substitution leaving group, wherein ring $C^{vi}$ can be fused with phenyl or substituted, the same as defined for $C^{ii}$.

The invention also provides a compound of the following formula

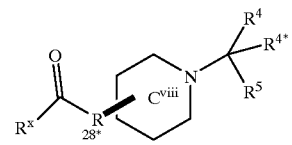

that can be used to synthesize a compound of the invention, wherein ring $C^{viii}$ can be fused with phenyl or substituted, the same as defined for ring $C^{ii}$. The invention also provides a method of synthesizing this compound, the method comprising reducing a compound of the following formula

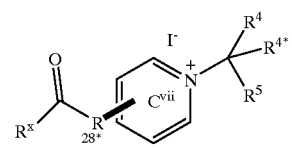

to reduce the double bonds in ring $C^{vii}$, wherein ring $C^{vii}$ can be fused with phenyl or substituted, the same as defined for ring $C^{ii}$.

The invention also provides a method of synthesizing a compound that can be used to synthesize the compound of the invention, the method comprising synthesizing a compound of formula

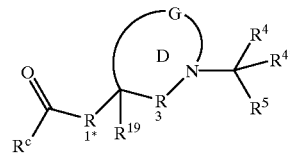

by reacting a compound of the formula

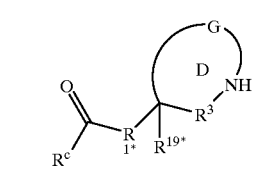

with a compound of the formula

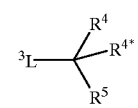

The invention also provides a method of synthesizing of a compound of the invention, the method comprising reacting a compound of formula

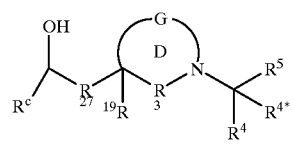

with Ar—Q wherein Ar is aryl which is substituted with an electron-withdrawing group or heteroaryl and is substituted with an electron-withdrawing group, and wherein Q is halide (preferably fluoro or chloro), to form

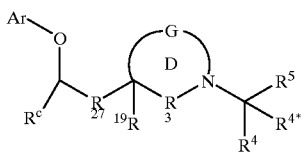

The invention also provides a method of synthesizing a compound that can be used to synthesize the compound of the invention, the method comprising synthesizing a compound of formula X:

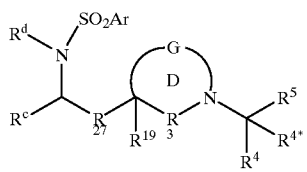

by reacting a compound of formula:

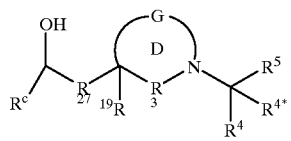

with $R^d NHSO_2Ar$, wherein Ar is aryl or heteroaryl, Preferably, the method further comprises converting the compound of formula X to:

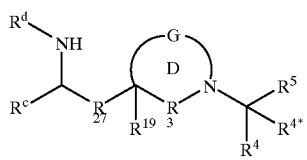

The invention also provides a method of synthesizing a compound that can be used to synthesize the compound of the invention, the method comprising reacting a compound of formula

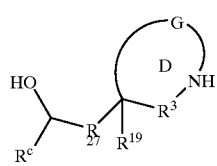

with a compound of formula

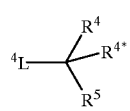

wherein L4 is a nucleophilic substitution leaving group, to form a compound of formula

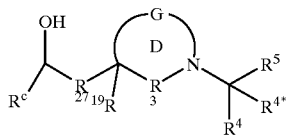

The invention also provides a method of synthesizing a compound that can be used to synthesize the compound of the invention, the method comprising synthesizing the compound of formula:

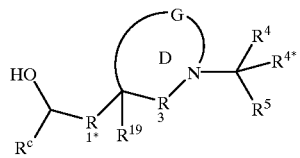

said synthesis comprising reducing the ketone of a compound of formula

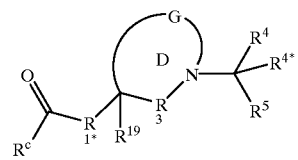

The invention also provides a compound of the following formula

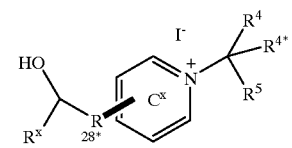

that can be used to synthesize a compound of the invention, wherein I⁻ is a negative counter-ion, wherein $R^{28}$ is the same as $R^1$ except that the bond to the ring is not a double bond, wherein ring $C^x$ can be fused with phenyl or substituted, the same as defined for ring $C^{ii}$. The invention also provides a method of synthesizing this compound, comprising reacting a compound of the formula

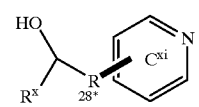

with a compound of the formula

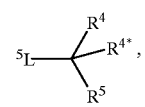

wherein $L^5$ is a nucleophilic substitution leaving group, wherein ring $C^{xi}$ can be fused with phenyl or substituted, the same as defined for $C^{ii}$.

The invention also provides a compound of the following formula

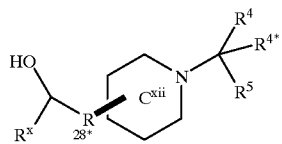

that can be used to synthesize a compound of the invention, wherein $R^{28}$ is the same as $R^1$ except that the bond to the ring is not a double bond, wherein ring $C^{xii}$ can be fused with phenyl or substituted, the same as defined for ring $C^{ii}$. The invention also provides a method of synthesizing this compound, the method comprising reducing a compound of the following formula

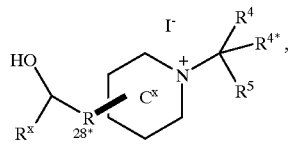

to reduce the double bonds in ring $C^x$, ring $C^x$ can be fused with phenyl or substituted, the same as defined for ring $C^{ii}$.

BRIEF DESCRIPTION OF THE DRAWING

FIGURE depicts several reactions that can be employed in the synthesis of the compounds of the invention.

DEFINITIONS

The following terms shall have the meaning set forth below:

accounting for ring heteroatoms
  If two rings are linked to form a bicyclic ring system, then a nitrogen located at one of the junctions is considered a heteroatom of each of the component rings.

excipient
  Excipients are pharmaceutically acceptable organic or inorganic carrier substances suitable for parenteral, enteral (e.g., oral or inhalation) or topical application that do not deletereiously react with the active compositions. Suitable pharmaceutically acceptable carriers include but are not limited to water, salt solutions, alcohols, gum arabic, benzyl alcohols, gelatine, carbohydrates such as lactose, amylose or starch, magnesium stearate, talc, silicic acid, hydroxymethylcellulose, polyvinylpyrrolidone, and the like.

effective amount
  The meaning of "effective amount" will be recognized by clinicians but includes amount effective to (1) reduce, ameliorate or eliminate one or more symptoms of the disease sought to be treated, (2) induce a pharmacological change relevant to treating the disease sought to be treated, or (3) prevent or lessen the frequency of occurrence of a disease.

neuronal cell death prevention
  Neuronal cell death is "prevented" if there is a reduction in the amount of cell death that would have been expected to have occurred but for the administration of a compound of the invention.

oxo substitution
  References to oxo as a "substituent" refer to "=O" substitutions.

DETAILED DESCRIPTION

The compounds of the invention are generally prepared according to one of the following synthetic schemes, although alternative schemes will be recognized by those of ordinary skill.

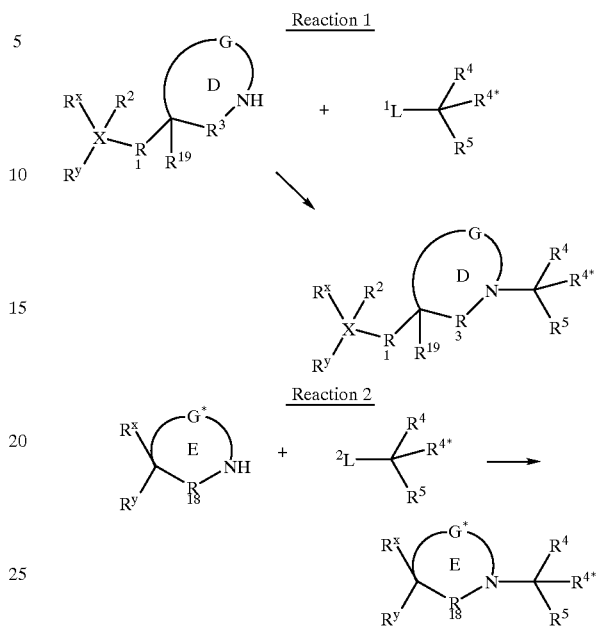

In Reaction 1 and Reaction 2, $L^1$ and $L^2$ are good nucleophilic substitution leaving groups such as a halide, especially a bromide, a tosylate, a brosylate (p-bromobenzenesulfonate), and the like. The reaction is preferably conducted in the presence of a base such as potassium carbonate or a tertiary amine such as diisopropylethylamine. Where the leaving group is a halide, the reaction can be conducted in the presence of an iodide salt such as potassium iodide. Suitable organic solvents include, for example, methanol, dioxane, acetonitrile or dimethyformamide. The reaction is favorably conducted at a temperature range of about 15° C. to about 40° C. Avoiding more elevated temperatures helps avoid producing the quaternary ammonium salt resulting from bis-alkylation.

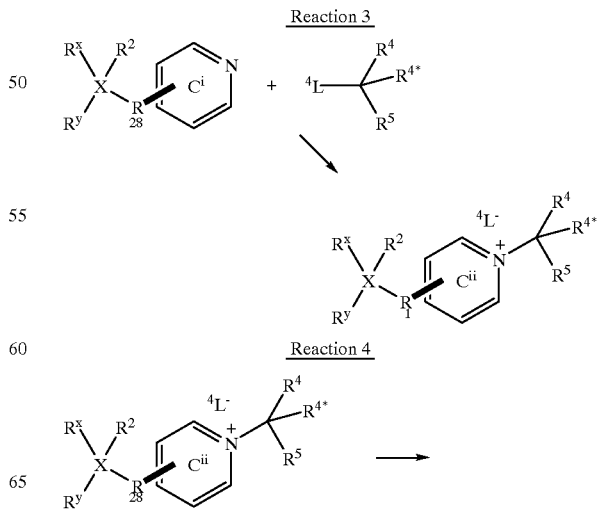

-continued

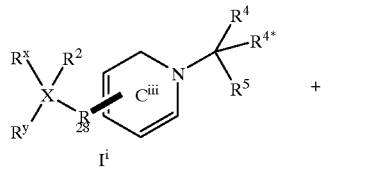

Cmpound $I^i$ can be reduced further, for instance in a Reaction 5 that produces:

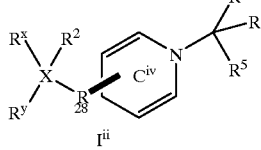

A further Reaction 6 can be used to fully reduce ring $C^v$. In the above-described Reactions 3 to 6, the bond between $R^1$ and the ring is either at the 2, 3 or 4 position of the ring. In the alkylation of Reaction 3, $L^4$ is a good nucleophilic substitution leaving group such as a halide, especially a bromide. Although not indicated above, the ring C can be substituted. Suitable organic solvents include, for example, those that effectively solubilize the starting materials and are unreactive to the alkylation reagent. Depending on the reactants, such solvents can include benzene, acetonitrile, tetrahydrofuran or ethanol. The reaction is favorably conducted at a temperature range of about 20° C. to about 100° C.

In Reactions 4 and 5, the ring C is reduced by one of a number of reduction procedures known in the art, such as, for instance, reaction with a metal hydride such as sodium borohydride. See R. M. Acheson, G. Paglietti, *J. Chem. Soc., Perkin I*, p. 45, 1976. It will be recognized that, while the above reaction schemes describe the separate formation of various partially reduced compounds such as $I^i$, $I^{ii}$ and $I^{iii}$, the ratio of these products and the ease with which they can be isolated will vary with each case, depending on such factors as the type of metal hydride used and the solvent used. In Reaction 6, the ring $C^v$ is further reduced by one of a number of reduction procedures known in the art, such as, for instance, hydrogenation in the presence of an appropriate hydrogenation catalyst. For example, in many cases the hydrogenation can be conducted with a Pd/C catalyst and in an alcohol solvent.

In Reaction 7, shown in the FIGURE, $R^c$ and $R^d$ are independently the same as defined for $R^x$. The starting material III can be synthesized, for instance, using the chemistry of Reaction 15 (similar to Reaction 1), as follows:

Reaction 15

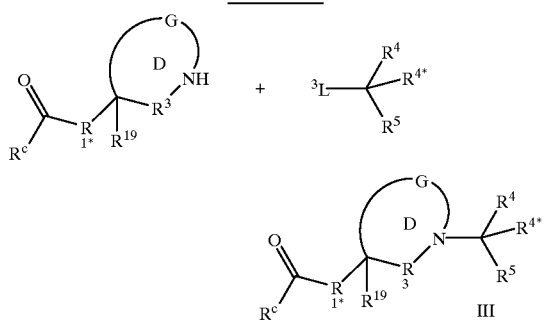

wherein $R^{1*}$ has the same definition as $R^1$ except that it does not include a nitrogen, does not include an oxygen linked to the above-illustrated carbonyl and does not include any double bonds conjugated with the above-illustrated carbonyl, and wherein $L^3$ is a good nucleophilic substitution leaving group such as a halide, especially a bromide, a tosylate, a brosylate (p-bromobenzenesulfonate), and the like.

In Reaction 7, shown in the FIGURE, $R^d$—$NH_2$ is reacted with III to form IV under conditions that effect a reductive alkylation. The reductive alkylation can be effected by several known methods (see, for example, "Reductive Alkylation," W. S. Emerson in *Organic Reactions*, Vol. 4, John Wiley & Sons, 1948, p. 174 et seq.) including reaction with hydrogen in the presence of a catalyst such as palladium on carbon, reaction with sodium cyanoborohydride or reaction with sodium triacetoxyborohydride when groups labile to catalytic hydrogenation are present. It will be recognized that an intermediate Schiff's base is formed in the reaction, which Schiff's base is reduced to form the linkage. The intermediate Schiff's base can be isolated and then reduced in a separate reaction. Solvent selection will vary with such factors as the solubility of the starting materials, the degree to which the solvent favors the dehydration reaction forming the Schiff's base, and the suitability of the solvent in the reduction process. Suitable solvents using catalytic hydrogenation to reduce the Schiff's base include ethanol. Suitable solvents using a borohydride to reduce the Schiff's base include alcoholic solvents such as methanol or ethanol. In some cases, a drying process can be employed during the reaction to promote the dehydration reaction that forms the Schiff's base that is reduced. Such drying processes include refluxing under conditions selected to remove water as an azeotrope or the use of molecular sieves or other drying reagents. Suitable reaction temperatures include the range from about 20° C. to the reflux temperature of the solvent employed.

Alternatively, IV can be synthesized via Reaction 16, shown in the FIGURE, by reacting $R^d$—$NH_2$ with X under the conditions described for Reaction 1 or Reaction 2. In another alternative, starting material $III^i$ is prepared as follows:

Reaction 17

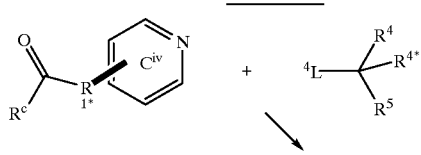

-continued

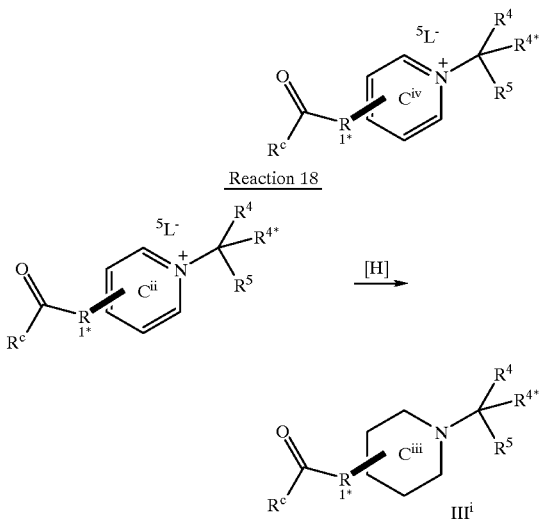

Reaction 18

These Reactions 17 and 18 use chemistry described above for Reactions 3 and 6, respectively. This compound III$^i$ can be substituted for III in Reactions 7, 8 and 12, shown in the FIGURE.

In Reaction 8, shown in the FIGURE, R$^e$ is independently the same as defined for R$^1$. In Reaction 8, III or III$^i$ is reacted with a organometallic reagent such as an aryllithium or an aryl or arylalkyl Grignard reagent to form V, as described, for instance, in Section 5.1.2 of Cary and Sundberg, Advanced Organic Chemistry, Part 2, Plenum, New York, 1977, pp. 170–180, and references cited therein. Those of ordinary skill will be aware that in some cases where R$^5$ includes an ester, the organometallic reagent may react with the ester group; in those such cases where the yield of the desired product is too low, the solvent, the organometallic reagent or the ester substitution can be varied.

In Reaction 9, shown in the FIGURE, V is subjected to conditions suitable for dehydration to form a double bond. Such conditions are, for instance, those described in H. Weiland, Ber. 45: 484 et seq. (1912), wherein V is refluxed with acetic anhydride. In the illustration, the double bond forms with the adjacent carbon atom of R$^{1*}$. The double bond will typically form with this orientation where R$^c$ and R$^e$ are aryl or heteroaryl and the adjacent carbon of R$^{1*}$ is saturated and not fully substituted, but other orientations are possible depending on the composition of R$^c$, R$^e$ and R$^{1*}$. In reaction 10, shown in the FIGURE, VI is is reduced, for instance using any of a number of known methods for reducing carbon-carbon double bonds, such as catalytic hydrogenation in the presence of an appropriate catalyst.

In reaction 11, shown in the FIGURE, V is acylated, for instance, with acetic anhydride in the presence of an acylation catalyst such as 4-dimethylaminopyridine.

In reaction 12, shown in the FIGURE, the ketone moiety of III or III$^i$ is reduced, for instance by any of a number of known methods for selectively reducing ketones, such as reaction with lithium tri-tert-butoxyaluminohydride. For reaction 13, shown in the FIGURE, the hydroxyl of IX is replaced by a leaving group L$^6$, wherein the leaving group is, for instance, chloro or bromo, by reacting IX with, for instance, thionyl chloride or thionyl bromide. For reaction 14, shown in the FIGURE, R$^f$ independently satisfies the definition of R$^x$. X is reacted with R$^f$OH in the presence of a base such as K$_2$CO$_3$ or sodium hydride. Alternatively, the thio-containing analog of XI can be synthesized by reacting X with R$^f$SH.

In reaction 19, IX is reacted with R$^d$NHSO$_2$Ar to yield XII, for instance for instance under the conditions of Mitzunobu reaction, and further converted into IV by reacton 20, analogously to the procedure described in J. R. Henry et al., Tetrahedron Letters 30: 5709–5712, 1989.

A number of other well-known synthetic approaches can be applied. For instance, acids can be formed by the hydrolysis of the corresponding esters. Amine derivatives can be formed by the alkylation of primary, secondary or tertiary amines. A number of double bond containing compounds can be hydrogenated to form the corresponding single bond.

Compounds of the invention may also be prepared by adapting the classical solution chemistries outlined above into solid-phase synthetic techniques. For example, R$^{13}$, R$^{15}$, R$^{16}$, R$^{17}$ and R$^{20}$ can be residues other than hydrogen representing functionalized resin or suitably selected. linker attached to functionalized resin. The linker and the functional group represented by R$^5$ should be stable under the conditions employed for the above-described reactions. The compounds of the invention where R$^{13}$, R$^{15}$, R$^{16}$, R$^{17}$ is R$^{20}$ is hydrogen, are then cleaved from the resin or the linker leaving the remainder of the molecule intact. For example, solid-phase synthesis of peptoids [oligo(N-substituted glycines)] using robotic synthesizer was described by Zuckermann et al., J. Am. Chem. Soc., 114, 0646–10647, (1992) and Spellmeyer et al, WO 95/04072). Under analogous conditions, acylation reaction of Rink amide polystyrene resin with bromoacetic acid in the presence of N,N'-diisopropylcarbodiimide followed by displacement of the bromine with the amine component of reaction 1 or reaction 2, and cleavage can provide N-substituted glycinamides (R$^{13}$ and R$^{14}$ are hydrogen).

In some cases, the chemistries outlined above may have to be modified, for instance by use of protective groups, to prevent side reactions due to reactive groups, such as reactive groups incorporated into heterocyclic rings or attached as substituents. Using the reactions described herein, hydrolysis of esters, alkylation of amines, or hydrogenation reactions, the following compounds of the invention have been synthesized:

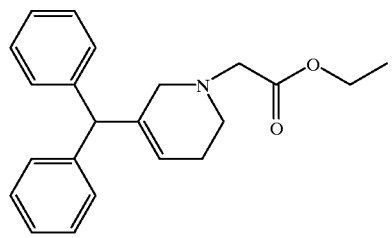

C1

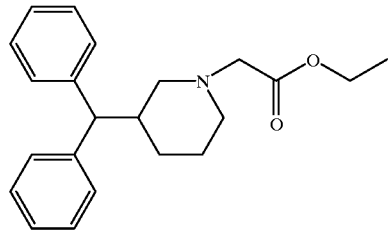

C2

C3
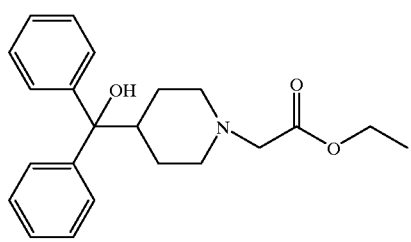
C4
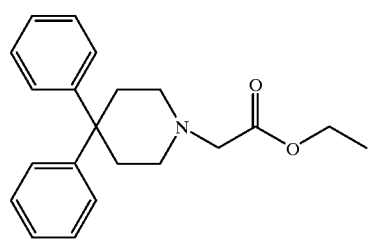
C5
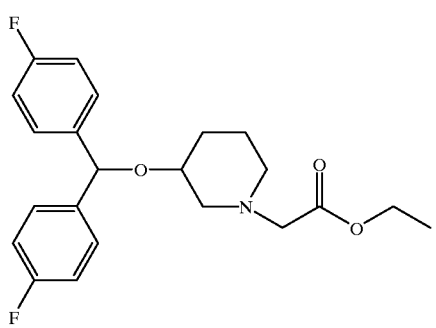
C6
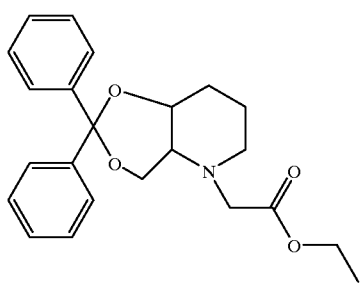
C7
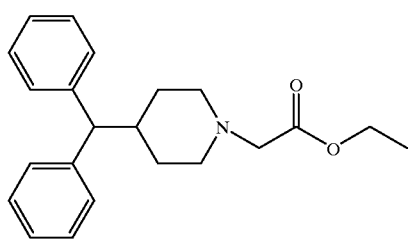
C8
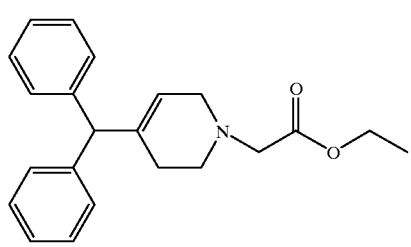
C9
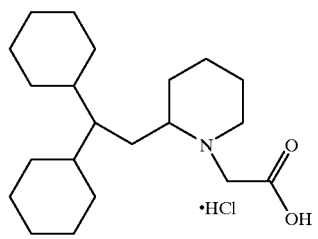
C10
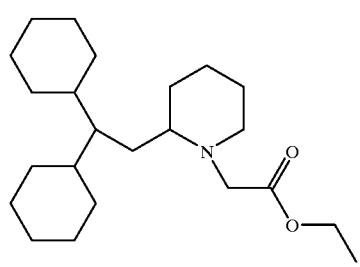
C11
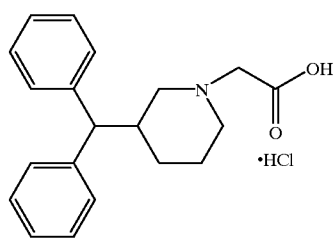
C12
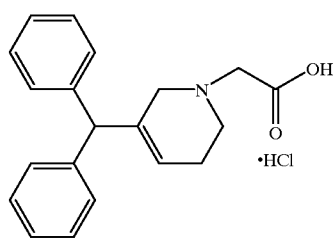
C13
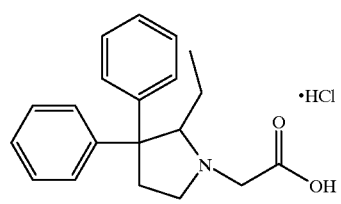
C14
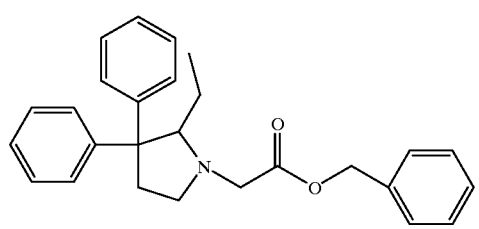

-continued

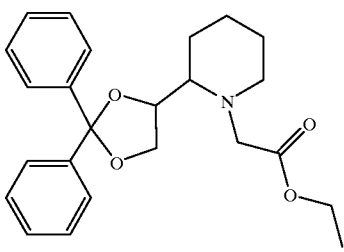

C15

It will be recognized that numerous salt forms of the compounds herein described are available and suitable for use in the invention or during the synthesis of compounds of the invention. The invention contemplates that in certain instances where stereoisomers are available that one such isomer can be more active than another; in such a case, it will be desirable to isolate the particular isomeric form. The invention, of course, encompasses both the particular stereoisomers and racemic mixtures. As described herein, chemical approaches, starting with for example commercially available, optically pure starting materials (or made using enantioselective reactions), can also used to synthesize optically pure versions of the compounds of the invention. It will be recognized that such optically pure compounds are within the invention. Enantiomeric excess ("ee") can be enhanced by purification techniques such as crystallization or chromatography on chiral supports. Enantiomeric excess can be quantitated by a number of analytic techniques including NMR, optical rotation measurements and appropriate chromatography.

Additional, related compounds are described in U.S. patent applications were filed concurrently with the parents hereof as U.S. Ser. No. 08/656,063 (Docket No. 317743-103, Ognyanov et al.) U.S. Ser. No. 08/655,912 (Docket No. 317743-106, Ognyanov et al.), U.S. Ser. No. 08/807,754 (PHARMACEUTICAL FOR TREATMENT OF NEUROLOGICAL AND NEUROPSYCHIATRIC DISORDERS, Docket No. 317743-103A, Ognyanov et al.) and U.S. Ser. No. 08/807,682 (PHARMACEUTICAL FOR TREATMENT OF NEUROPSYCHIATRIC AND NEUROLOGICAL DISORDERS, Docket No. 317743-106A, Ognyanov et al.), which applications are also incorporated herein by reference in their entirety. Further incorporated by reference in their entirety are U.S. application Ser. No. 08/655,847 (Docket No. 317743-107, Ognyanov et al.) and U.S. application Ser. No. 08/807,681 (Docket No. 317743-107A, Ognyanov et al.), the parents of the present application.

It will be recognized that some combinations of components of the compounds of the invention will be less stabile than others. For example, when the ring D or the ring E is fully saturated any two ring heteroatoms should typically be separated by at least two ring carbons to maintain stability. The compounds having sufficient stability to be useful as pharmaceuticals are of greater usefulness.

In a preferred embodiment, the D ring or the E ring is substituted with at most one of aryl or heteroaryl.

The glycine transporter genes and their respective gene products are responsible for the reuptake of glycine from the synaptic cleft into presynaptic nerve endings or glial cells, thus terminating the action of glycine. Neurological disorders or conditions associated with improperly controlled glycine receptor activity, or which could be treated with therapeutic agents that modulate glycine receptor activity, include spasticity (Becker, FASEB Journal, 4, 2767–2774 (1990)) and pain realization (Yaksh, Pain, 37, 111–123 (1989)). Additionally, glycine interacts at N-methyl-D-aspartate (NMDA) receptors, which have been implicated in learning and memory disorders and certain clinical conditions such as epilepsy, Alzheimer's and other cognition-related diseases, and schizophrenia. See Rison and Stanton, Neurosci. Biobehav. Rev. 19, 533–552 (1995); Danysz et al., Behavioral Pharmacol., 6, 455–474 (1995).

Compounds that inhibit GlyT-1 mediated glycine transport will increase glycine concentrations at NMDA receptors, which receptors are located in the forebrain, among other locations. This concentration increase elevates the activity of NMDA receptors, thereby alleviating schizophrenia and enhancing cognitive function. Alternatively, compounds that interact directly with the glycine receptor component of the NMDA receptor can have the same or similar effects as increasing or decreasing the availability of extracellular glycine caused by inhibiting or enhancing GlyT-1 activity, respectively. See, for example, Pitkänen et al., Eur. J. Pharmacol., 253, 125–129 (1994); Thiels et al., Neuroscience, 46, 501–509 (1992); and Kretschmer and Schmidt, J. Neurosci., 16, 1561–1569 (1996). Compounds that inhibit GlyT-2 mediated glycine transport will increase glycine concentrations at receptors located primarily in the brain stem and spinal cord, where glycine acts as an inhibitor of synaptic transmission. These compounds are effective against epilepsy, pain and spasticity, myospasm and other such conditions. See, for example, Becker, FASEB J., 4, 2767–2774 (1990) and Yaksh, Pain, 37, 111–123 (1989).

The compounds of the invention are, for instance, administered orally, sublingually, rectally, nasally, vaginally, topically (including the use of a patch or other transdermal delivery device), by pulmonary route by use of an aerosol, or parenterally, including, for example, intramuscularly, subcutaneously, intraperitoneally, intraarterially, intravenously or intrathecally. Administration can be by means of a pump for periodic or continuous delivery. The compounds of the invention are administered alone, or are combined with a pharmaceutically-acceptable carrier or excipient according to standard pharmaceutical practice. For the oral mode of administration, the compounds of the invention are used in the form of tablets, capsules, lozenges, chewing gum, troches, powders, syrups, elixirs, aqueous solutions and suspensions, and the like. In the case of tablets, carriers that are used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the compounds of the invention are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. For pulmonary administration, diluents and/or carriers will be selected to be appropriate to allow the formation of an aerosol.

Suppository forms of the compounds of the invention are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycols of various molecular weight and fatty acid esters of polyethylene glycol. See, Remington's Pharmaceutical Sciences, 16th Ed., Mack Publishing, Easton, Pa., 1980, pp. 1530–1533 for further discussion of suppository dosage forms. Analogous gels or cremes can be used for vaginal, urethral and rectal administrations.

Numerous administration vehicles will be apparent to those of ordinary skill in the art, including without limitation slow release formulations, liposomal formulations and polymeric matrices.

Examples of pharmaceutically acceptable acid addition salts for use in the present invention include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic and arylsulphonic acids, for example. Examples of pharmaceutically acceptable base addition salts for use in the present invention include those derived from non-toxic metals such as sodium or potassium, ammonium salts and organoamino salts such as triethylamine salts. Numerous appropriate such salts will be known to those of ordinary skill.

The physician or other health care profesional can select the appropriate dose and treatment regimen based on the subject's weight, age, and physical condition. Dosages will generally be selected to maintain a serum level of compounds of the invention between about 0.01 μg/cc and about 1000 μg/cc, preferably between about 0.1 μg/cc and about 100 μg/cc. For parenteral administration, an alternative measure of preferred amount is from about 0.01 mg/kg to about 10 mg/kg, more preferably from about 0.1 mg/kg to about 1 mg/kg, will be administered. For oral administrations, an alternative measure of preferred administration amount is from about 0.1 mg/kg to about 10 mg/kg, more preferably from about 0.1 mg/kg to about 1 mg/kg. For administrations in suppository form, an alternative measure of preferred administration amount is from about 0.1 mg/kg to about 10 mg/kg, more preferably from about 0.1 mg/kg to about 1 mg/kg.

For use in assaying for activity in inhibiting glycine transport, eukaryokic cells, preferably QT-6 cells derived from quail fibroblasts, have been transfected to express one of the three known variants of human GlyT-1, namely GlyT-1a, GlyT-1b or GlyT-1c or human GlyT-2. The sequences of these GlyT-1 transporters are described in Kim et al., *Molec. Pharm.* 45: 608–617, 1994, excepting that the sequence encoding the extreme N-terminal of GlyT-1a was merely inferred from the corresponding rat-derived sequence. This N-terminal protein-encoding sequence has now been confirmed to correspond to that inferred by Kim et al. The sequence of the human GlyT-2 is described by Albert et al., U.S. application Ser. No. 08/700,013, filed Aug. 20, 1996, which is incorporated herein by reference in its entirety. Suitable expression vectors include pRc/CMV (Invitrogen), Zap Express Vector (Stratagene Cloning Systems, LaJolla, Calif.; hereinafter "Stratagene"), pBk/CMV or pBk-RSV vectors (Stratagene), Bluescript II SK ± Phagemid Vectors (Stratagene), LacSwitch (Stratagene), pMAM and pMAM neo (Clontech), among others. A suitable expression vector is capable of fostering expression of the included GlyT DNA in a suitable host cell, preferably a non-mammalian host cell, which can be eukaryotic, fungal, or prokaryotic. Such preferred host cells include amphibian, avian, fungal, insect, and reptilian cells.

As discussed above, the compounds of the invention have a number of pharmacological actions. The relative effectiveness of the compounds can be assessed in a number of ways, including the following:

comparing the activity mediated through GlyT-1 and GlyT-2 transporters. This testing identifies compounds (a) that are more active against GlyT-1 transporters and thus more useful in treating or preventing schizophrenia, increasing cognition and enhancing memory or (b) that are more active against GlyT-2 transporters and thus more useful in treating or preventing epilepsy, pain, spasticity or myospasm.

testing for NMDA receptor binding. This test establishes whether there is sufficient binding at this site, whether antagonist or agonist activity, to warrant further examination of the pharmacological effect of such binding.

testing the activity of the compounds in enhancing or diminishing calcium fluxes in primary neuronal tissue culture. A test compound that increases calcium flux either (a) has little or no antagonist activity at the NMDA receptor and should not affect the potentiation of glycine activity through GlyT-1 transporter inhibition or (b), if marked increases are observed over GlyT-1 inhibitors used for comparison and that have little direct interaction with NMDA receptors, then the compound is a receptor agonist. In either of the above-described cases, the test confirms activity in treating or preventing schizophrenia, increasing cognition, or enhancing memory. In contrast, a test compound that decreases calcium flux has a net effect wherein receptor antagonist activity predominates over any activity the compound has in increasing glycine activity through inhibiting glycine transport. In this case, the test confirms activity in limiting or preventing the cell damage and cell death arising after stroke or other ischemia-inducing conditions, or in limiting or preventing the cell damage associated with neurodegenerative diseases.

All animal methods of treatment or prevention described herein are preferably applied to mammals, most preferably humans.

The following examples further illustrate the present invention, but of course, should not be construed as in any way limiting its scope.

EXAMPLE 1

Synthesis of 3-bis(4-fluorophenyl) methoxypiperidin-1-yl acetic acid ethyl ester (Compound C5)

A mixture of 0.170 g (0.5 mmol) of 3-bis(4-fluorophenyl) methoxypiperidine [prepared in three steps from 3-hydroxypiperidine hydrochloride (Aldrich) using the synthetic scheme described by E. Falch, P. Krogsgaard-Larsen, *Eur. J. Med. Chem.* 1991, 26, 69–78, for the synthesis of 3-diphenylmethoxypiperidine], 0.092 g (0.55 mmol) ethyl bromoacetate (Aldrich) and 0.276 g (2 mmol) potassium carbonate in 1 ml acetonitrile was stirred under argon for 20 hours. The reaction mixture was filtered, the solvent evaporated and the residue purified by preparative TLC with 30% ethyl acetate in hexanes to give 0.150 g (yield 77%) 3-bis (4-fluorophenyl) methoxypiperidin-1-yl acetic acid ethyl ester (compound C5) as an oil. NMR spectra of the product showed: $^1$H NMR (CDCl$_3$, 300 MHz) δ 7.60–7.35 (m, 4 H), 7.35–7.00 (m, 4 H), 5.72 (s, 1 H), 4.38 (q, 2 H), 3.90–3.65 (m, 1 H), 3.42 (br. s, 2 H), 3.25 (d, 1 H), 2.97 (d, 1 H), 2.42 (dt, 2 H), 2.17 (d, 1 H), 2.00–1.80 (m, 1 H), 1.70 (dt, 1 H), 1.60–1.50 (m, 1 H), 1.46 (t, 3 H), $^{13}$C NMR (CDCl$_3$, 75 MHz) δ 170.16, 163.52, 160.27, 138.14, 138.11, 128.50, 128.40, 115.13, 114.85, 79.30, 72.45, 60.27, 59.31, 57.83, 52.80, 30.06, 23.12, 14.01.

EXAMPLE 2

Additional Syntheses for Reactions 1 and 2

Compounds were synthesized using Reaction 1 or Reaction 2, as follows:

| Compound | Reaction | Amine | Reagent | Solvent | Yield |
| --- | --- | --- | --- | --- | --- |
| C3 | 1 | 2 | A | X | 38% |
| C4 | 2 | 1 | A | X | 58% |
| C6 | 2 | 3 | A | X | 86% |
| C10 | 1 | 4 | A | X | 89% |
| C14 | 2 | 5 | B | X | 65% |
| C15 | 1 | 6 | A | X | 67% |

Amine: 1) 4,4-diphenylpiperidine (J. M. Wetzel et al., *J. Med. Chem,,* 38: 1579–1581, 1995); 2) α,α-diphenyl-4-piperidinomethanol (Acros, Pittsburgh, Pa.); 3) 2,2-diphenyl-4A,5,6,7,8,8A-hexahydro-4H-1,3-dioxino[5,4-b]pyridine (Sigma-Aldrich Library of Rare Chemicals); 4) perhexiline maleate [2-(2,2-dicyclohexylethyl)piperidyne] (Sigma, St. Louis); 5) 3,3-diphenyl-2-ethylpyrrolidine [prepared by sodium borohydride reduction of 3,3-diphenyl-2-ethyl-1-pyrroline (Sigma-Aldrich Library of Rare Chemicals)]; 6) 2,2-diphenyl-1,3-dioxolan-4-yl)piperidine hydrochloride (Sigma-Aldrich Library of Rare Chemicals)].

Reagent: A) ethyl bromoacetate (Aldrich); B) benzyl 2-bromoacetate (Aldrich).

Solvent: X acetonitrile.

EXAMPLE 3

Synthesis of 3-Diphenylmethyl-1,2,3,6,-tetrahydropyridin-1-yl acetic acid ethyl ester (Compound C1)

Step 1: A mixture of 0.490 g (2 mmol) 3-diphenylmethylpyridine (Sigma-Aldrich Library of Rare Chemicals) and 0.334 g (4 mmol) ethyl bromoacetate (Aldrich) in 2 ml acetonitrile was heated under reflux for 1 hour. The solvent was evaporated, the residue suspended in diethyl ether and filtered to give 0.8 g 1-ethoxycarbonylmethyl-3-diphenylmethylpyridinium bromide as a yellow powder. $^1$H NMR (CD$_3$OD, 300 MHz) δ 8.87 (d, 1 H), 8.77 (s, 1 H), 8.42 (d, 1 H), 8.10 (dd, 1 H), 7.50–7.10 (m, 10 H), 5.96 (s, 1 H), 5.55 (s, 2 H), 4.28 (q, 2 H), 1.29 (t, 3 H).

Step 2: To an ice cooled solution of 0.206 g (0.5 mmol) 1-ethoxycarbonylmethyl-3-diphenylmethylpyridinium bromide (from step 1) was added 0.034 g (0.92 mmol) sodium borohydride in small portions with stirring over one hour. The solvent was evaporated, the residue dissolved in diethyl ether, washed with water and dried with magnesium sulphate. After evaporation of the solvent, the residue was chromatographed on silica gel column with 30% ethyl acetate in hexanes to give 0.107 g (64%) 3-diphenylmethyl-1,2,3,6-tetrahydropyridin-1-yl acetic acid ethyl ester (compound C1) as a pale yellow oil. NMR spectra showed:

$^1$H NMR (CDCl$_3$, 300 MHz) δ 7.40–7.10 (m, 10 H), 5.22 (br. s,1 H), 4.61 (s, 1 H), 4.12 (q, 2 H), 3.25 (s, 2 H), 3.03 (s, 2 H), 2.68 (t, 2 H), 2.22 (br. s, 2 H), 1.19 (t, 3 H); $^{13}$C NMR (CDCl$_3$ 75 MHz) δ 170.24, 141.86, 137.89, 129.11, 128.10, 126.19, 123.24, 60.31, 58.79, 56.24, 55.13, 49.51, 25.64, 14.05. El-MS: 335 (10, M$^+$, C$_{22}$H$_{25}$NO$_2$), 262 (50).

EXAMPLE 4

Additional Syntheses

Compound C8 was prepared in 29% yield by sodium borohydride reduction of the corresponding quaternary salt of 4diphenylmethylpyridine (Aldrich) using the methodology of Example 3.

EXAMPLE 5

Hydrogenation of Compound C1 to form 3-diphenylmethylpiperidin-1-yl acetic acid ethyl ester (Compound C2)

0.041 g (0.122 mmol) or 3-diphenylmethyl-1,2,3,6-tetrahydropyridin-1-yl acetic acid ethyl ester (compound C1) was hydrogenated with 0.040 g 10% Pd/C in 4 ml ethanol at 40 psi for 6 hours at room temperature. The mixture was filtered from the catalyst through celite and the solvent evaporated to give 0.038 g (yield 93%) 3-diphenylmethylpiperidin-1-yl acetic acid ethyl ester (compound C2) as an oil. NMR spectra of the product showed: $^1$H NMR (CDCl$_3$, 300 MHz) δ 7.40–7.10 (m, 10 H), 4.11 (q, 2 H), 3.52 (d, 1 H), 3.10 (s, 2 H), 2.87 (d, 1 H), 2.72 (d, 1 H), 2.65–2.40 (m, 1 H), 2.20–2.00 (m, 1 H), 1.87 (t, 1H), 1.70–1.50 (m, 3 H), 1.17 (t, 3 H), 1.00–0.8 (m, 1 H); $^{13}$C NMR (CDCl$_3$, 75 MHz) δ 168.89, 142.11, 141.81, 126.92, 126.90, 126.36, 126.28, 124.58, 124.50, 58.78, 58.47, 57.29, 55.34, 52.05, 37.97, 27.86, 23.58, 12.57. El-MS: 337 (5, M$^+$, C$_{22}$H$_{27}$NO$_2$), 264 (70).

EXAMPLE 6A

Additional Syntheses

Compound C7 is prepared by hydrogenation of compound C8 using the methodology of Example 5.

EXAMPLE 6B

Additional Syntheses using the Procedure of Example 6A

Compound C13 was prepared by hydrogenation of compound C14 (using the methodology of Example 6A), followed by acidification with HCl.

EXAMPLE 6C

Synthesis of 2-(2,2-Dicyclohexylethyl)piperidin-1-yl acetic acid hydrochloride (Compound C9)

To a solution of 0.413 g (1.136 mmol) 2-(2,2-dicyclohexylethyl)piperidin-1-yl acetic acid ethyl ester (Compound C10) in 4 ml methanol was added 8 ml 1N sodium hydroxide and the mixture was heated under reflux for one hour. The reaction mixture was concentrated to half volume, acidified with 4N hydrochloric acid, and extracted four times with methylene chloride. The combined extracts were dried and evaporated to give 0.400 g (yield 95%) 2-(2,2-dicyclohexylethyl)piperidin-1-yl) acetic acid hydrochloride (Compound C9).

EXAMPLE 6D

Additional Syntheses using the Procedure of Example 6C

Compound C11 was prepared by hydrolysis of Compound C2, followed by acidification with HCl.

Compound C12 was prepared by hydrolysis of Compound C1, followed by acidification with HCl.

EXAMPLE 7

Preparation of Cells Expressing GlyT-1 and GlyT-2

This example sets forth methods and materials used for growing and transfecting QT-6 cells.

QT-6 cells were obtained from American Type Culture Collection (Accession No. ATCC CRL-1708). Complete QT-6 medium for growing QT-6 is Medium 199 (Sigma Chemical Company, St. Louis, Mo.; hereinafter "Sigma") supplemented to be 10% tryptose phosphate; 5% fetal bovine serum (Sigma); 1% penicillin-streptomycin (Sigma); and 1% sterile dimethylsulfoxide (DMSO; Sigma). Other solutions required for growing or transfecting QT-6 cells included:

DNA/DEAE Mix: 450 μl TBS, 450 μl DEAE Dextran (Sigma), and 100 μl of DNA (4 μg) in TE, where the DNA includes GlyT-1a, GlyT-1b, GlyT-1c, or GlyT-2, in a suitable expression vector. The DNA used was as defined below.

PBS: Standard phosphate buffered saline, pH 7.4 including 1 mM $CaCl_2$ and 1 mM $MgCl_2$ sterilized through 0.2μ filter.

TBS: One ml of Solution B, 10 ml of Solution A; brought to 100 ml with distilled $H_2O$; filter-sterilized and stored at 4° C.

TE: 0.01 M Tris, 0.001 M EDTA, pH 8.0.

DEAE dextran: Sigma, #D-9885. A stock solution was prepared consisting of 0.1% (1 mg/ml) of the DEAE dextran in TBS. The stock solution was filter sterilized and frozen in 1 ml aliquots.

Chloroquine: Sigma, #C-6628. A stock solution was prepared consisting of 100 mM chloroquine in $H_2O$. The stock solution was filter-sterilized and stored in 0.5 ml aliquots, frozen.

Solution A (10×):

| | |
|---|---|
| NaCl | 8.00 g |
| KCl | 0.38 g |
| Tris base | 3.00 g |
| $Na_2HPO_4$ | 0.20 g |

The solution was adjusted to pH 7.5 with HCl, brought to 100.0 ml with distilled $H_2O$, and filter-sterilized and stored at room temperature.

Solution B (100×):

| | |
|---|---|
| $CaCl_2.2H_2O$ | 1.5 g |
| $MgCl_2.6H_2O$ | 1.0 g |

The solution was brought to 100 ml with distilled $H_2O$, and filter-sterilized; the solution was then stored at room temperature.

HBSS: 150 mM NaCl, 20 mM HEPES, 1 mM $CaCl_2$, 10 mM glucose, 5 mM KCl, 1 mM $MgCl_2.H_2O$; adjusted with NaOH to pH 7.4.

Standard growth and passaging procedures used were as follows: Cells were grown in 225 ml flasks. For passaging, cells were washed twice with warm HBSS (5 ml each wash). Two ml of a 0.05% trypsin/EDTA solution was added, the culture was swirled, then the trypsin/EDTA solution was aspirated quickly. The culture was then incubated about 2 minutes (until cells lift off), then 10 ml of QT-6 media was added and the cells were further dislodged by swirling the flask and tapping its bottom. The cells were removed and transferred to a 15 ml conical tube, centrifuged at 1000 xg for 10 minutes, and resuspended in 10 ml of QT-6 medium. A sample was removed for counting, the cells were then diluted further to a concentration of $1 \times 10^5$ cells/ml using QT-6 medium, and 65 ml of the culture was added per 225 ml flask of passaged cells.

Transfection was accomplished using cDNA's prepared as follows:

The rat GlyT-2 (rGlyT-2) clone used contains the entire sequence of rGlyT-2 cloned into pBluescript SK+ (Stratagene) as an Eco RI-Hind III fragment, as described in Liu et al., *J. Biol. Chem.* 268, 22802–22808 (1993). GlyT-2 was then subcloned into the pRc/RSV vector as follows: A PCR fragment corresponding to nucleotides 208 to 702 of the rGlyT-2 sequence was amplified by PCR using the oligonucleotide: 5'GGGGGAAGCTTATGGATTGCAGT-GCTCC 3' as the 5' primer and the oligonucleotide: 5' GGGGGGGTACCCAACACCACTGTGCTCTG 3' as the 3' primer. This created a Hind III site immediately upstream of the translation start site. This fragment, which contained a Kpn I site at the 3' end, along with a Kpn 1-Pvu II fragment containing the remainder of the coding sequence of rGlyT-2, were cloned into pBluescript SK+ previously digested with Hind III and Sma I, in a three part ligation. A Hind III-Xba 1 fragment from this clone was then subcloned into the pRc/RSV vector. The resulting construct contains nucleotides 208 to 2720 of the rGlyT-2 nucleic acid in the pRc/RSV expression vector.

The human GlyT-1a (hGlyT-1a) clone used contains the sequence of hGlyT-1a from nucleotide position 183 to 2108 cloned into the pRc/CMV vector (Invitrogen, San Diego, Calif.) as a Hind III-Xba 1 fragment as described in Kim et al., *Mol. Pharmacol.* 45, 608–617, 1994. This cDNA encoding GlyT-1a actually contained the first 17 nucleotides (corresponding to the first 6 amino acids) of the GlyT-1a sequence from rat. To determine whether the sequence of human GlyT-1a was different in this region, the 5' region of hGlyT-1a from nucleotide 1 to 212 was obtained by rapid amplification of cDNA end using the 5' RACE system supplied by Gibco BRL (Gaithersburg, Md.). The gene specific primer: 5' CCACATTGTAGTAGATGCCG 3' corresponding to nucleotides 558 to 539 of the hGlyT-1a sequence, was used to prime cDNA synthesis from human brain mRNA, and the gene specific primer: 5' GCAAACTG-GCCGAAGGAGAGCTCC 3', corresponding to nucleotides 454 to 431 of the hGlyT-1a sequence, was used for PCR amplification. Sequencing of this 5' region of GlyT-1a confirmed that the first 17 nucleotides of coding sequence are identical in human and rat GlyT-1a.

The human GlyT-1b (hGlyT-1b) clone used contains the sequence of hGlyT-1b from nucleotide position 213 to 2274 cloned into the pRc/CMV vector as a Hind III-Xba I fragment as described in Kim et al., *Mol. Pharmacol.*, 45, 608–617, 1994.

The human GlyT-1c (hGlyT-1c) clone used contains the sequence of hGlyT-1c from nucleotide position 213 to 2336 cloned into the pRc/CMV vector (Invitrogen) as a Hind III-Xba I fragment as described in Kim et al., *Mol. Pharmacol.*, 45, 608–617, 1994. The Hind III-Xba fragment of hGlyT-1c from this clone was then subcloned into the pRc/RSV vector. Transfection experiments were performed with GlyT-1c in both the pRc/RSV and pRc/CMV expression vectors.

The following four day procedure for the tranfectons was used:

On day 1, QT-6 cells were plated at a density of $1\times10^6$ cells in 10 ml of complete QT-6 medium in 100 mm dishes.

On day 2, the media was aspirated and the cells were washed with 10 ml of PBS followed by 10 ml of TBS. The TBS was aspirated, and then 1 ml of the DEAE/DNA mix was added to the plate. The plate was swirled in the hood every 5 minutes. After 30 minutes, 8 ml of 80 μM chloroquine, in QT-6 medium was added and the culture was incubated for 2.5 hours at 37° C. and 5% $CO_2$. The medium was then aspirated and the cells were washed two times with complete QT-6 media, then 100 ml complete QT-6 media was added and the cells were returned to the incubator.

On day 3, the cells were removed with trypsin/EDTA as described above, and plated into the wells of 96-well assay plates at approximately $2\times10^5$ cells/well.

On day 4, glycine transport was assayed as described in Example 8.

EXAMPLE 8

Assay of Transport Via GlyT-1 or GlyT-2 Transporters

This example illustrates a method for the measurement of glycine uptake by transfected cultured cells.

Transient GlyT-transfected cells grown in accordance with Example 7 were washed three times with HEPES buffered saline (HBS). The cells were then incubated 10 minutes at 37° C., after which a solution was added containing 50 nM [$^3$H]glycine (17.5 Ci/mmol) and either (a) no potential competitor, (b) 10 mM nonradioactive glycine or (c) a concentration of a candidate drug. A range of concentrations of the candidate drug was used to generate data for calculating the concentration resulting in 50% of the effect (e.g., the $IC_{50}$s, which are the concentrations of drug inhibiting glycine uptake by 50%). The cells were then incubated another 10 minutes at 37° C., after which the cells were aspirated and washed three times with ice-cold HBS. The cells were harvested, scintillant was added to the cells, the cells were shaken for 30 minutes, and the radioactivity in the cells was counted using a scintillation counter. Data were compared between the same cells contacted or not contacted by a candidate agent, and between cells having GlyT-1 activity versus cells having GlyT-2 activity, depending on the assay being conducted.

EXAMPLE 9

Assay of Binding to NMDA Receptors

This example illustrates binding assays to measure interaction of compounds with the glycine site on the NMDA receptor.

Direct binding of [$^3$H]glycine to the NMDA-glycine site was performed according to the method of Grimwood et al., *Molecular Pharmacology*, 41, 923–930 (1992); Yoneda et al., *J. Neurochem*, 62, 102–112 (1994).

Preparation of membranes for the binding test required application of a series of standard methods. Unless otherwise specified, tissues and homogenates were kept on ice and centrifugations were conducted at 4° C. Homogenizations were conducted with an effort to minimize resulting rise in tissue/homogenate temperature. The membrane preparation included the following steps:

1. Sacrifice and decapitate four rats; remove cortices and hippocampi.
2. Homogenize tissue in twenty volumes of 0.32 M sucrose/5 mM Tris-Acetate (pH 7.4) with 20 strokes of a glass/teflon homogenizer.
3. Centrifuge issue at 1000×g, 10 minutes. Save supernatant Resuspend pellet in small volume of buffer and homogenize again. Centrifuge the homogenized pellet and combine the supernatant with the previous supernatant.
4. Centrifuge the combined supernatants at 40,000×g, for 30 minutes. Discard the supernatant.
5. Resuspend the pellet in 20 volumes of 5 mM Tris-Acetate (pH 7.4). Stir the suspension on ice for one hour. Centrifuge the suspension at 40,000×g for 30 minutes. Discard the supernatant and freeze the pellet for at least 24 hours.
6. Resuspend the pellet from step 5 in Tris Acetate buffer (5 mM, pH 7.4) containing 0.1% saponin (w/v; Sigma Chemical Co., St. Louis) to a protein concentration of 1 mg/ml. Leave on ice for 20 minutes. Centrifuge the suspension at 40,000×g for 30 minutes. Resuspend the pellet in saponin-free buffer and centrifuge again. Resuspend the pellet in Tris-Acetate buffer at a concentration of 10 mg/ml and freeze in aliquots.
7. On day three, remove an aliquot of membranes and thaw on ice. Dilute the suspension into 10 ml Tris-Acetate buffer and centrifuge at 40,000×g for 30 minutes. Repeat the wash step twice more for a total of 3 washes. Resuspend the final pellet at a concentration of 1 mg/ml in glycine-free Tris-Acetate buffer.

The binding test was performed in eppendorf tubes containing 150 μg of membrane protein and 50 nM [$^3$H]glycine in a volume of 0.5 ml. Non-specific binding was determined with 1 mM glycine. Drugs were dissolved in assay buffer (50 mM Tris-acetate, pH 7.4) or DMSO (final concentration of 0.1%). Membranes were incubated on ice for 30 minutes and bound radioligand was separated from free radioligand by filtration on Whatman GF/B glass fiber filters or by centrifugation (18,000×g, 20 min). Filters or pellet was washed three times quickly with ice-cold 5 mM Tris-acetate buffer. Filters were dried and placed in scintillation tubes and counted. Pellets were dissolved in deoxycholate/NaOH (0.1 N) solution overnight, neutralized and radioactivity was determined by scintillation counting.

A second binding test for the NMDA-glycine site used [$^3$H]dichlorokynurenic acid (DCKA) and membranes prepared as above. See, Yoneda et al., *J. Neurochem.*, 60,634–645 (1993). The binding assay was performed as described for [$^3$H]glycine above except that [$^3$H]DCKA was used to label the glycine site. The final concentration of [$^3$H]DCKA was 10 nM, and the assay was performed for 10 minutes on ice.

A third binding test used for the NMDA-glycine site used indirect assessment of affinity of ligands for the site by measuring the binding of [$^3$H]MK-801 (dizocilpine). See, Palmer and Burns, *J. Neurochem.*, 62, 187–196 (1994). Preparation of membranes for the test was the same as above. The binding assay allowed separate detection of antagonists and agonists.

The third binding test was operated to identify antagonists as follows: 100 μg of membranes were added to wells of a 96-well plate, along with glutamate (10 μM) and glycine (200 nM) and various concentrations of the ligand to be tested. The assay was started by the addition of 5 nM [$^3$H]MK-801 (23.9 Ci/mmol), which binds to the ion channel associated with NMDA receptors. The final volume of the assay was 200 μl. The assay was performed for 1 hour at room temperature. Bound radioactivity was separated from free by filtration, using a TOMTEC harvester. Antagonist activity was indicated by decreasing radioactivity associated with the NMDA receptor with increasing concentration of the tested ligand.

The third binding test was operated to identify agonists by performing the test as above, except that the concentration of glycine was 200 nM. Agonist activity was indicated by increasing radioactivity associated with the NMDA receptor with increasing concentration of the tested ligand.

EXAMPLE 10

Assay of Calcium Flux

This example illustrates a protocol for measuring calcium flux in primary neuronal calls.

The calcium flux measurement is performed in primary neuronal cell cultures, which are prepared from rat fetal cortices dissected from pregnant rats using standard procedures and techniques that require sterile dissecting equipment, a microscope and defined medium. The protocol used was adapted from Lu et al., *Proc. Nat'l. Acad. Sci. USA*, 88, 6289–6292 (1991). Defined medium is prepared in advance in accordance with the following recipe:

| Components | Source (catalogue #) | Final Concentration |
|---|---|---|
| D-glucose | Sigma (G-7021) | 0.6% |
| transferrin | Sigma (T-2252) | 100 μg/ml |
| insulin | Sigma (I-5500) | 25 μg/ml |
| progesterone | Sigma (P-6149) | 20 nM |
| putrescine | Sigma (P-7505) | 60 μM |
| selenium | Sigma (S-5261) | 30 nM |
| pen-strep▲ | GIBCO (15070-014) | 0.5 U-0.5 μg/ml |
| L-glutamine* | GIBCO (25030-016) | 146 mg/l |
| MEM° | GIBCO (11095 or 11090) | 500 ml/l |
| F-12 | GIBCO (11765) | 500 ml/l |

▲pen-strep: 5,000 U/ml penicillin and 5,000 μg/ml streptomycin
*add only when MEM without L-glutamine is used
°with L-glutamine or without L-glutamine, respectively Before starting the dissection, issue culture plates were treated with polylysine (100 μg/ml for at least 30 minutes at 37° C.) and washed with distilled water. Also, a metal tray containing two sets of sterile crude dissecting equipment (scissors and tweezers) and several sets of finer dissecting tools was autoclaved. A pair of scissors and tweezers were placed into a sterile beaker with 70% alcohol and brought to the dissecting table. A petri dish with cold phosphate buffered saline (PBS) was placed on ice next to the place of dissection.

A pregnant rat (E15 or 16 on arrival from Hilltop Lab Animals (Scottdale, Pa.), E17 or 18 at dissection) was placed in a CO$_2$/dry ice chamber until it was unconscious. The rat was removed, pinned to a backing, the area of dissection was swabbed with 70% alcohol, and skin was cut and removed from the area of interest. A second pair of scissors was used to cut through and remove the prenatal pups in their sacs. The string of sacs was placed into the cold PBS and transported to a sterile hood.

The prenatal pups were removed from the sacs and decapitated. The skulls were then removed and the brains were carefully dislodged and placed into a clean petri dish with cold PBS. At this point, it was necessary to proceed with a dissecting microscope. The brain was turned so that the cortices were contacting the plate and the tissue between the dissector and the cortex (striatum and other brain parts) was scooped out. The hippocampus and olfactory bulb were cut away from the cortex. Then the tissue was turned over and the meninges were removed with tweezers. The remaining issue (cortex) was placed in a small petri dish with defined media.

The tissue was chopped with a scalpel and then triturated with a glass pipet that had been fire polished. The chopped, triturated tissue was then transferred to a sterile plastic tube and continued to be triturated with a glass pipet with a finer opening. Cells were counted in a suitable counting chamber. Cells were plated at roughly 40,000 cells/well in 100 μl of defined medium for 96-well plates, 200,000 cells/well in 500 μl in 24well plates, 400,000 cells/well in 1 ml in 12-well plates, 1.5×10$^8$ cells/35 mm dish in 1.5 ml and 10×10$^8$ cells/100 mm dish in 10 ml. To inhibit glia growth, cultures were treated with 100 μM 5-flouro-2-deoxyuridine (FDUR, Sigma (F-0503)) or 50/μM uridine (Sigma (U-3003)) and 50 μM FDUR.

The cortical cultures for the standard calcium flux assay were grown in 24-well plates in the defined medium described above for 7 days and fed once with serum containing media (10% heat inactivated fetal calf serum, 0.6% glucose in MEM) by exchanging half of the medium. Cultures were used after 12 days of incubation in vitro. The cultures were rinsed three times with HCSS (i.e. HEPES-buffered control salt solution, containing 120 mM NaCl, 5.4 mM KCl, 1.8 mM CaCl$_2$ 25 mM HEPES, and 15 mM glucose, in HPLC water and adjusted to pH 7.4 by NaOH, which was also made in HPLC water). In the third wash, the culture was incubated at 37° C. for 20 to 30 minutes.

Solutions containing $^{45}$Ca$^{++}$ (5000 dpm/ml) and drugs for testing or controls were prepared in HCSS. Immediately before the above $^{45}$Ca$^{++}$ solutions were added, cultures were washed twice with HCSS, and 250 μl of $^{45}$Ca$^{++}$ solution per well was added, one plate at a time. The cultures were incubated for 10 minutes at room temperature, rinsed three times with HCSS, and 1 ml scintillation liquid per well was added, followed by shaking for at least 15 minutes. Retained radioactivity was counted in a scintillation counter.

While this invention has been described with an emphasis upon preferred embodiments, it will be obvious to those of ordinary skill in the art that variations in the preferred compositions and methods may be used and that it is intended that the invention may be practiced otherwise than as specifically described herein. Accordingly, this invention includes all modifications encompassed within the spirit and scope of the invention as defined by the claims that follow.

What is claimed:

1. A compound of formula I or II:

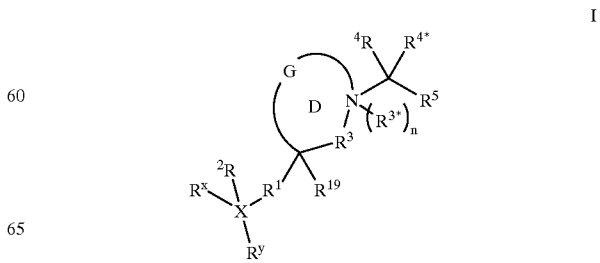

-continued

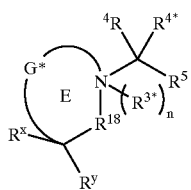

II or a pharmaceutically acceptable salt thereof,
wherein:

(1) X is nitrogen or carbon, and $R^2$ is not present when X is nitrogen;

(2) $R^2$ (a) is hydrogen, (C1–C6) alkyl, (C1–C6) alkoxy, cyano, (C2–C7) alkanoyl, aminocarbonyl, (C1–C6) alkylaminocarbonyl or dialkylaminocarbonyl wherein each alkyl is independently C1 to C6, (b) comprises (where $R^1$ is not —O—$R^8$ or —S—$R^{8*}$) hydroxy, fluoro, chloro, bromo or (C2–C7) alkanoyloxy, (c) forms a double bond with an adjacent carbon or nitrogen from one of either $R^1$, $R^{xb}$ or $R^{yb}$, (d) is oxygen forming an oxa linkage with $R^1$ or integrated into ring E (see, for example, Compound C6) or (e) is $R^{2a}$ linked by $R^{2b}$ to X;

($2^i$) $R^x$ is a ring-containing structure $R^{xa}$ linked by $R^{xb}$ to X;

($2^{ii}$) $R^y$ is a ring-containing structure $R^{ya}$ linked by $R^{yb}$ to X;

($2^{iii}$) $R^{xa}$, $R^{ya}$ and $R^{2a}$, are independently aryl, heteroaryl, adamantyl or a 5 to 7-membered non-aromatic ring having from 0 to 2 heteroatoms selected from the group consisting of oxygen, sulfur and nitrogen, wherein:
  (a) aryl is phenyl or naphthyl,
  (b) heteroaryl comprises a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon,
  (c) each of $R^{xa}$, $R^{ya}$ and $R^{2a}$ can be independently substituted with one of $R^q$, $R^rO$— or $R^sS$—, wherein Rq, Rr and Rs are independently aryl, heteroaryl, adamantyl or a 5 to 7-membered non-aromatic ring as these structures are defined for $R^{xa}$, and
  (d) $R^{xa}$, $R^{ya}$, $R^{2a}$, $R^q$, $R^r$ and $R^s$ can be substituted or additionally substituted with substituents selected from the group consisting of fluoro, chloro, bromo, nitro, hydroxy, cyano, trifluoromethyl, amidosulfonyl which can have up to two independent (C1–C6) N-alkyl substitutions, adamantyl, (C1–C12) alkyl, (C1–C12) alkenyl, amino, (C1–C6) alkylamino, dialkylamino wherein each alkyl is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two independent (C1–C6) alkyl, (C1–C6) alkylsulfonyl, amidino that can independently substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl, wherein:

(i) the substitutions of $R^{xa}$, $R^{ya}$ and $R^{2a}$ can be combined to form a second bridge between two of $R^{xa}$, $R^{ya}$ and $R^{2a}$ comprising (1) (C1–C2) alkyl or alkenyl, which can be independently substituted with one or more (C1–C6) alkyl, (2) sulfur, (3) oxygen, (4) amino, which can be substituted for hydrogen with one (C1–C6) alkyl, (5) carbonyl, (6) —CH$_2$C(=O)—, which can be substituted for hydrogen with up to two independent (C1–C6) alkyl, (7) —C(=O)—O—, (8) —CH$_2$—O—, which can be substituted for hydrogen with up to two independent (C1–C6) alkyl, (9) —C(=O)—N($R^{24}$)—, wherein $R^{24}$ is hydrogen or (C1–C6) alkyl, (10) —CH$_2$—NH—, which can be substituted for hydrogen with up to three (C1–C6) alkyl, or (11) —CH=N—, which can be substituted for hydrogen with (C1–C6) alkyl, or wherein two of $R^{xa}$, $R^{ya}$ and $R^{2a}$ can be directly linked by a single bond;

($2^{iv}$) $R^{xb}$ and $R^{2b}$ are independently a single bond or (C1–C2) alkylene;

($2^v$) $R^{yb}$ is a single bond, oxa, (C1–C2) alkylene, ethenylene or —CH= (where the double bond is with X), thia, methyleneoxy or methylenethio, or either —N($R^6$)— or —CH$_2$—N($R^{6*}$)—, wherein $R^6$ and $R^{6*}$ are hydrogen or (C1–C6) alkyl, wherein when X is nitrogen X is not bonded to another heteroatom;

(3) $R^1$ comprises: a single bond or double bond; a straight-chained (C1–C3) aliphatic group; or (where X is carbon and $R^{yb}$ does not include a heteroatom attached to X) —O—$R^8$ or —S—$R^{8*}$, wherein either $R^8$ or $R^{8*}$ is a single bond, (C1–C3) alkylene or (C2–C3) alkenylene and O or S is bonded to X:
  wherein $R^1$ can be substituted with up to one hydroxy, up to one (C1–C6) alkoxy or up to one (C2–C7) alkanoyloxy, with up to two independent (C1–C6) alkyl, with up to one oxo, up to one (C2–C6) alkylidene, with the proviso that the hydroxy, alkoxy, alkanoyloxy, oxo substituents are not bonded to a carbon that is bonded to a nitrogen or oxygen, or (where $R^1$ is —O—$R^8$ and X is carbon) an oxa linkage to X forming a 1,3-dioxolane,
  wherein the alkyl or alkylidene substituents of $R^1$ can be linked to form a 3 to 7-membered non-aromatic ring, and
  wherein if X is nitrogen, X is linked to $R^1$ by a single bond and the terminal carbon of $R^1$ that links $R^1$ to N is saturated;

(4) n is 0 or 1, and where if n is 1, $R^{3*}$ is either (C1–C6) alkyl (with the attached nitrogen having a positive charge) or oxygen (forming an N-oxide) and X is carbon;

(5) wherein ring D is a 6-membered ring, a 6-membered ring substituted with a 3 to 6-membered spiro ring, or a 6-membered ring fused with a 5 to 6-membered ring, wherein the fused ring lacking the illustrated tertiary nitrogen can be aromatic, with the proviso that the ring atoms include no quaternary nitrogens:
  wherein the carbon and nitrogen ring atoms of ring D can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C1–C6) alkoxy, oxo, hydroxycarbonyl, aryl wherein the aryl is as defined for $R^a$ or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms; and wherein $R^1$, $R^3$ and G are such that at least two atoms separate X and the illustrated ring nitrogen;

(6) wherein ring E is a 6-membered ring, a 6-membered ring substituted with a 3 to 6-membered spiro ring, or a 6-membered ring fused with a 5 to 6-membered ring, wherein the fused ring lacking the illustrated tertiary nitrogen can be aromatic, with the proviso that the ring atoms include no quaternary nitrogens:

wherein the carbon and nitrogen ring atoms of ring E can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl (C–C6) alkoxy, oxo, hydroxycarbonyl, (C1–C6) alkoxycarbonyl, aryl wherein the aryl is as defined for $R^a$, or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms; and wherein G* and $R^{18}$ are such that at least two atoms separate the illustrated ring nitrogen from the carbon linked to $R^x$ and $R^y$;

(7) $R^{19}$ (a) forms a double bond with $R^1$, $R^3$ or G, (b) is hydrogen (c) is (C1–C3) alkyl or alkylene, or (d) is incorporated into a fused ring;

(8) $R^4$ and $R^{4*}$ are independently hydrogen or (C1–C6) alkyl or one of $R^4$ and $R^{4*}$ can be (C1–C6) hydroxyalkyl; and (9) R5 is $(CO)NR^{13}R^{14}$, $(CO)OR^{15}$, $(CO)SR^{16}$, $(SO_2)NR^{17}R^{18}$, $(PO)(OR^{19})(OR^{20})$, $(CR^{22})(OR^{23})(OR^{24})$, CN or tetrazol-5-yl, wherein $R^{13}$, $R^{14}$, $R^{15}$, $R^{16}$, $R^{17}$, $R^{18}$, $R^{19}$ and $R^{20}$ are independently hydrogen, (C1–C8) alkyl which can include a (C3–C8) cycloalkyl, wherein the carbon linked to the oxygen of R15 or the sulfur of R16 has no more than secondary branching and, (C2–C6) hydroxyalkyl, aminoalkyl where the alkyl is C2 to C6 and the amino can be substituted with up to two independent (C1–C6) alkyls, arylalkyl wherein the alkyl is C1–C6, heteroarylalkyl wherein the alkyl is C1 to C6, aryl or heteroaryl, $R^{22}$ is hydrogen or $OR^{25}$ and $R^{23}$, $R^{24}$ and $R^{25}$ are (C1–C6) alkyl, phenyl, benzyl, acetyl or, where $R^{22}$ is hydrogen, the alkyls of $R^{23}$ and $R^{24}$ can be combined to include 1,3-dioxylane or 1,3-dioxane:

wherein the aryl is phenyl or naphthyl and the heteroaryl is a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon;

wherein the aryl, heteroaryl, aryl of arylalkyl or the heteroaryl of heteroarylalkyl can be substituted with substituents selected from the group consisting of fluoro, chloro, bromo, nitro, cyano, trifluoromethyl, amidosulfonyl which can have up to two independent (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two independent (C1–C6) alkyl, (C1–C6) alkylsulfonyl, amidino that can substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl; and wherein $R^{13}$ and $R^{14}$ together with the nitrogen can form a 5 to 7-membered ring that can contain one additional heteroatom selected from oxygen and sulfur;

wherein when (i) D is piperidine, (ii) $R^2$ is OH, (iii) $R^x$ is $R^{xa}$, and (iv) $R^y$ is $R^{ya}$, then $R^{xa}$ and $R^{ya}$ are not phenyl, phenyl substituted with fluoro, chloro, bromo, hydroxy, trifluoromethyl, C1–C8 alkyl, C1–C6 alkoxy, or not pyridyl, and $R^5$ is not (CO)$NR^{13}R^{14}$ or $(CO)OR^{15}$ when $R^{13}$, $R^{14}$, and $R^{15}$ are independently hydrogen, C1–C8 alkyl, phenyl, or phenyl substituted with fluoro, chloro, bromo, C1–C6 alkyl or C1–C6 alkoxy; and wherein when (i) D is piperidine, (ii) X is carbon, (iii) $R^1$ is $OR^8$, (iv) $R^5$ is $(CO)OR^{15}$, (v) $R^x$ is $R^{xa}$ and (vi) $R^y$ is $R^{ya}$, then $R^{xa}$ and $R^{ya}$ are not both phenyl or phenyl substituted with fluoro, chloro, bromo, C1–C4 alkyl or C1–C4 alkoxy and $R^{15}$ is not hydrogen or C1–C4 alkoxy.

2. The compound of claim 1, wherein (A) at least one of $R^{xa}$, $R^{ya}$ and $R^{2a}$ is substituted with fluoro, chloro, bromo, hydroxy, trifluoromethyl, trifluoromethoxy, nitro, cyano, (C3–C8) alkyl, $R^q$, $R^rO$—, $R^sS$—, or (B) the ring structures of $R^{xa}$, $R^{ya}$ and $R^{2a}$, including substituents thereto, otherwise include at least two aromatic ring structures that together include from 15 to 20 ring atoms.

3. The compound of claim 2, wherein at least one of $R^{xa}$, $R^{ya}$ and $R^{2a}$ is substituted with fluoro, trifluoromethyl, trifluoromethoxy, nitro, cyano, or (C3–C8) alkyl.

4. The compound of claim 1, wherein at least one of $R^{xa}$, $R^{ya}$ and $R^{2a}$ is substituted with $R^q$, $R^rO$—, or $R^sS$—.

5. The compound of claim 1, wherein an aryl or heteroaryl of at least one of $R^{xa}$, $R^{ya}$ and $R^{2a}$ is phenyl.

6. A compound of formula I or II:

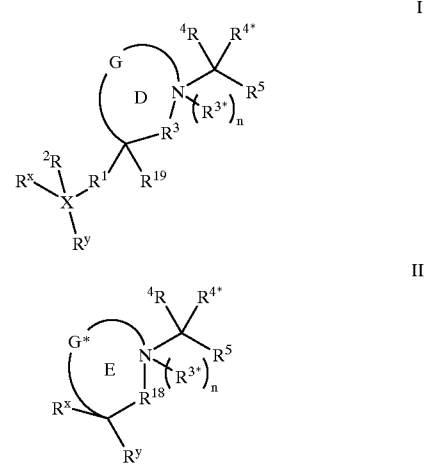

or a pharmaceutically acceptable salt thereof, wherein:
(1) X is nitrogen or carbon, and $R^2$ is not present when X is nitrogen;
(2) $R^2$ (a) is hydrogen, (C1–C6) alkyl, (C1–C6) alkoxy, cyano, (C2–C7) alkanoyl, aminocarbonyl, (C1–C6) alkylaminocarbonyl or dialkylaminocarbonyl wherein each alkyl is independently C1 to C6, (b) comprises (where $R^1$ is not —O—$R^8$ or —S—$R^{8*}$) hydroxy, fluoro, chloro, bromo or (C2–C7) alkanoyloxy, (c) forms a double bond with an adjacent carbon or nitrogen from one of either $R^1$, $R^{xb}$ or $R^{yb}$, (d) is oxygen forming an oxa linkage with $R^1$ or integrated into ring E (see, for example, Compound C6) or (e) is $R^{2a}$ linked by $R^{2b}$ to X;
($2^i$) $R^x$ is a ring-containing structure $R^{xa}$ linked by $R^{xb}$ to X;
($2^{ii}$) $R^y$ is a ring-containing structure $R^{ya}$ linked by $R^{yb}$ to X;
($2^{iii}$) $R^{xa}$, $R^{ya}$ and $R^{2a}$, are independently aryl, heteroaryl, adamantyl or a 5 to 7-membered non-aromatic ring having from 0 to 2 heteroatoms selected from the group consisting of oxygen, sulfur and nitrogen, wherein:
  (a) aryl is phenyl or naphthyl,
  (b) heteroaryl comprises a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon,
  (c) each of $R^{xa}$, $R^{ya}$ and $R^{2a}$ can be independently substituted with one of $R^q$, $R^rO$— or $R^sS$—, wherein Rq, Rr and Rs are independently aryl, heteroaryl, adamantyl or a 5 to 7-membered non-aromatic ring as these structures are defined for $R^{xa}$, and
  (d) $R^{xa}$, $R^{ya}$, $R^{2a}$, $R^q$, $R^r$ and $R^s$ can be substituted with substituents selected from the group consisting of fluoro, chloro, bromo, nitro, hydroxy, cyano, trifluoromethyl, amidosulfonyl which can have up to two independent (C1–C6) N-alkyl substitutions, adamantyl, (C1–C12) alkyl, (C1–C12) alkenyl, amino, (C1–C6) alkylamino, dialkylamino wherein each alkyl is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two independent (C1–C6) alkyl, (C1–C6) alkylsulfonyl, amidino that can independently substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl wherein:
    (i) the substitutions of $R^{xa}$, $R^{ya}$ and $R^{2a}$ can be combined to form a second bridge between two of $R^{xa}$, $R^{ya}$ and $R^{2a}$ comprising (1) (C1–C2) alkyl or alkenyl which can be independently substituted with one or more (C1–C6) alkyl (2) sulfur, (3) oxygen, (4) amino, which can be substituted for hydrogen with one (C1–C6) alkyl, (5) carbonyl, (6) —CH$_2$C(=O)—, which can be substituted for hydrogen with up to two independent (C1–C6) alkyl (7) —C(=O)—O—, (8) —CH$_2$—O—, which can be substituted for hydrogen with up to two independent (C1–C6) alkyl, (9) —C(=O)—N($R^{24}$)—, wherein $R^{24}$ is hydrogen or (C1–C6) alkyl, (10) —CH$_2$—NH—, which can be substituted for hydrogen with up to three (C1–C6) alkyl, or (11) —CH=N—, which can be substituted for hydrogen with (C1–C6) alkyl, or wherein two of $R^{xa}$, $R^{ya}$ and $R^{2a}$ can be directly linked by a single bond;
($2^{iv}$) $R^{xb}$ and $R^{2b}$ are independently a single bond or (C1–C2) alkylene;
($2^v$) $R^{yb}$ is oxa, methyleneoxy, thia, methylenethia;
(3) $R^1$ comprises: a single bond or double bond; a straight-chained (C1–C3) aliphatic group; or (where X is carbon and $R^{yb}$ does not include a heteroatom attached to X) —O—$R^8$ or —S—$R^{8*}$, wherein either $R^8$ or $R^{8*}$ is a single bond, (C1–C3) alkylene or (C2–C3) alkenylene and O or S is bonded to X:
  wherein $R^1$ can be substituted with up to one hydroxy, up to one (C1–C6) alkoxy or up to one (C2–C7) alkanoyloxy, with up to two independent (C1–C6) alkyl, with up to one oxo, up to one (C1–C6) alkylidene, with the proviso that the hydroxy, alkoxy, alkanoyloxy, oxo substituents are not bonded to a carbon that is bonded to a nitrogen or oxygen, or (where $R^1$ is —O—$R^8$ and X is carbon) an oxa linkage to X forming a 1,3-dioxolane,
  wherein the alkyl or alkylidene substituents of $R^1$ can be linked to form a 3 to 7-membered non-aromatic ring, and
  wherein if X is nitrogen, X is linked to $R^1$ by a single bond and the terminal carbon of $R^1$ that links $R^1$ to N is saturated;
(4) n is 0 or 1, and where if n is 1, $R^{3*}$ is either (C1–C6) alkyl (with the attached nitrogen having a positive charge) or oxygen (forming an N-oxide) and X is carbon;
(5) wherein ring D is a 6-membered ring, a 6-membered ring substituted with a 3 to 6-membered spiro ring, or a 6-membered ring fused with a 5 to 6-membered ring, wherein the fused ring lacking the illustrated tertiary nitrogen can be aromatic, with the proviso that the ring atoms include no quaternary nitrogens:
  wherein the carbon and nitrogen ring atoms of ring D can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C1–C6) alkoxy, oxo, hydroxycarbonyl, aryl wherein the aryl is as defined for $R^a$ or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms; and
  wherein $R^1$, $R^3$ and G are such that at least two atoms separate X and the illustrated ring nitrogen;
(6) wherein ring E is a 6-membered ring, a 6-membered ring substituted with a 3 to 6-membered spiro ring, or a 6-membered ring fused with a 5 to 6-membered ring, wherein the fused ring lacking the illustrated tertiary nitrogen can be aromatic:
  wherein the carbon and nitrogen ring atoms of ring E can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C–C6) alkoxy, oxo, hydroxycarbonyl, (C1–C6) alkoxycarbonyl, aryl wherein the aryl is as defined for $R^a$ or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms; and wherein G* and $R^{18}$ are such that at least two atoms separate the illustrated ring nitrogen from the carbon linked to $R^x$ and $R^y$;

(7) $R^{19}$ (a) forms a double bond with $R^1$, $R^3$ or G, (b) is hydrogen (c) is (C1–C3) alkyl or alkylene, or (d) is incorporated into a fused ring;

(8) $R^4$ and $R^{4*}$ are independently hydrogen or (C1–C6) alkyl, or one of $R^4$ and $R^{4*}$ can be (C1–C6) hydroxyalkyl; and (9) R5 is $(CO)NR^{13}R^{14}$, $(CO)OR^{15}$, $(CO)SR^{16}$, $(SO_2)NR^{17}R^{18}$, $(PO)(OR^{19})(OR^{20})$, $(CR^{22})(OR^{23})(OR^{24})$, CN or tetrazol-5-yl, wherein $R^{13}$, $R^{14}$, $R^{15}$, $R^{16}$, $R^{17}$, $R^{18}$, $R^{19}$ and $R^{20}$ are independently hydrogen, (C1–C8) alkyl which can include a (C3–C8) cycloalkyl, wherein the carbon linked to the oxygen of R15 or the sulfur of R16 has no more than secondary branching and, (C2–C6) hydroxyalkyl, aminoalkyl where the alkyl is C2 to C6 and the amino can be substituted with up to two independent (C1–C6) alkyls, arylalkyl wherein the alkyl is C1–C6, heteroarylalkyl wherein the alkyl is C1 to C6, aryl or heteroaryl, $R^{22}$ is hydrogen or $OR^{25}$ and $R^{23}$, $R^{24}$ and $R^{25}$ are (C1–C6) alkyl, phenyl, benzyl, acetyl or, where $R^{22}$ is hydrogen, the alkyls of $R^{23}$ and $R^{24}$ can be combined to include 1,3-dioxylane or 1,3-dioxane:

wherein the aryl is phenyl or naphthyl and the heteroaryl is a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon;

wherein the aryl, heteroaryl, aryl of arylalkyl or the heteroaryl of heteroarylalkyl can be substituted with substituents selected from the group consisting of fluoro, chloro, bromo, nitro, cyano, trifluoromethyl, amidosulfonyl which can have up to two independent (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two independent (C1–C6) alkyl, (C1–C6) alkylsulfonyl, amidino that can substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl; and wherein $R^{13}$ and $R^{14}$ together with the nitrogen can form a 5 to 7-membered ring that can contain one additional heteroatom selected from oxygen and sulfur.

7. The compound of claim 6, wherein $R^{yb}$ is oxa or thia.

8. The compound of claim 1, wherein $R^5$ is $(CO)NR^{13}R^{14}$, $(CO)OR^{15}$ or $(CO)SR^{16}$.

9. The compound of claim 8, wherein $R^{15}$ is (C2–C6) alkyl, (C2–C4) hydroxyalkyl, phenyl, phenylalkyl wherein the alkyl is C1–C3, or aminoalkyl where the alkyl is C2–C6 and the amino can be substituted with up to two independent (C1–C3) alkyls, wherein the phenyl or the phenyl of phenylalkyl can be substituted.

10. The compound of claim 8, wherein $R^{15}$ is hydrogen.

11. The compound of claim 1, wherein $R^4$ is hydrogen, methyl or hydroxymethyl and $R^{4*}$ is hydrogen.

12. A compound of FIG. I or II:

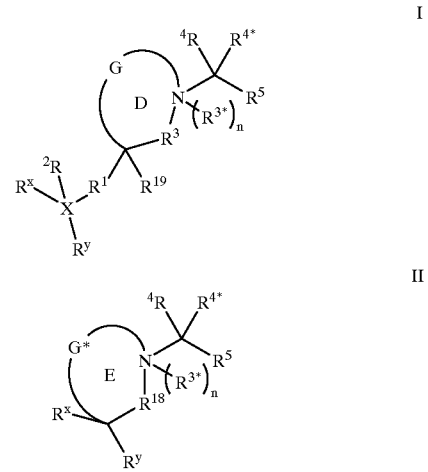

or a pharmaceutically acceptable salt thereof, wherein:

(1) X is nitrogen or carbon, and $R^2$ is not present when X is nitrogen;

(2) $R^2$ (a) is hydrogen, (C1–C6) alkyl, (C1–C6) alkoxy, cyano, (C2–C7) alkanoyl aminocarbonyl, (C1–C6) alkylaminocarbonyl or dialkylaminocarbonyl wherein each alkyl is independently C1 to C6, (b) comprises (where $R^1$ is not —O—$R^8$ or —S—$R^{8*}$) hydroxy, fluoro, chloro, bromo or (C2–C7) alkanoyloxy, (c) forms a double bond with an adjacent carbon or nitrogen from one of either $R^1$, $R^{xb}$ or $R^{yb}$, (d) is oxygen forming an oxa linkage with $R^1$ or integrated into ring E (see, for example, Compound C6) or (e) is $R^{2a}$ linked by $R^{2b}$ to X;

($2^i$) $R^x$ is a ring-containing structure $R^{xa}$ linked by $R^{xb}$ to X;

($2^{ii}$) $R^y$ is a ring-containing structure $R^{ya}$ linked by $R^{yb}$ to X;

($2^{iii}$) $R^{xa}$, $R^{ya}$ and $R^{2a}$, are independently aryl, heteroaryl, adamantyl or a 5 to 7-membered non-aromatic ring having from 0 to 2 heteroatoms selected from the group consisting of oxygen, sulfur and nitrogen, wherein:

(a) aryl is phenyl or naphthyl, (b) heteroaryl comprises a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon, (c) each of $R^{xa}$, $R^{ya}$ and $R^{2a}$ can be independently substituted with one of $R^q$, $R'O$— or $R^sS$—, wherein Rq, Rr and Rs are independently aryl, heteroaryl, adamantyl or a 5 to 7-membered non-aromatic ring as these structures are defined for $R^{xa}$, and (d) $R^{xa}$, $R^{ya}$, $R^{2a}$, $R^q$, $R^r$ and $R^s$ can be substituted with substituents selected from the group consisting of fluoro, chloro, bromo, nitro, hydroxy, cyano, trifluoromethyl amidosulfonyl which can have up to two independent (C1–C6) N-alkyl substitutions, adamantyl, (C1–C12) alkyl, (C1–C12) alkenyl amino, (C1–C6) alkylamino, dialkylamino wherein each alkyl is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl aminocarbonyl that can be substituted for hydrogen with up to two independent (C1–C6) alkyl, (C1–C6) alkylsulfonyl, amidino that can independently substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl, wherein:

(i) the substitutions of $R^{xa}$, $R^{ya}$ and $R^{2a}$ can be combined to form a second bridge between two of $R^{xa}$, $R^{ya}$ and $R^{2a}$ comprising (1) (C1–C2) alkyl or alkenyl, which can be independently substituted with one or more (C1–C6) alkyl, (2) sulfur, (3) oxygen, (4) amino, which can be substituted for hydrogen with one (C1–C6) alkyl, (5) carbonyl, (6) —CH$_2$C(=O)—, which can be substituted for hydrogen with up to two independent (C1–C6) alkyl, (7) —C(=O)—O—, (8) —CH$_2$—O—, which can be substituted for hydrogen with up to two independent (C1–C6) alkyl, (9) —C(=O)—N($R^{24}$)—, wherein $R^{24}$ is hydrogen or (C1–C6) alkyl, (10) —CH$_2$—NH—, which can be substituted for hydrogen with up to three (C1–C6) alkyl, or (11) —CH=N—, which can be substituted for hydrogen with (C1–C6) alkyl, or wherein two of $R^{xa}$, $R^{ya}$ and $R^{2a}$ can be directly linked by a single bond;

(2$^{iv}$) $R^{xb}$ and $R^{2b}$ are independently a single bond or (C1–C2) alkylene;

(2$^v$) $R^{yb}$ is a single bond, oxa, (C1–C2) alkylene, ethenylene or —CH= (where the double bond is with X), thia, methyleneoxy or methylenethio, or either —N($R^6$)— or —CH$_2$—N($R^{6*}$)—, wherein $R^6$ and $R^{6*}$ are hydrogen or (C1–C6) alkyl, wherein when X is nitrogen X is not bonded to another heteroatom;

(3) $R^1$ comprises: a single bond or double bond; a straight-chained (C1–C3) aliphatic group; or (where X is carbon and $R^{yb}$ does not include a heteroatom attached to X) —O—$R^8$ or —S—$R^{8*}$, wherein either $R^8$ or $R^{8*}$ is a single bond, (C1–C3) alkylene or (C2–C3) alkenylene and O or S is bonded to X:

wherein $R^1$ can be substituted with up to one hydroxy, up to one (C1–C6) alkoxy or up to one (C2–C7) alkanoyloxy, with up to two independent (C1–C6) alkyl, with up to one oxo, up to one (C1–C6) alkylidene, with the proviso that the hydroxy, alkoxy, alkanoyloxy, oxo substituents are not bonded to a carbon that is bonded to a nitrogen or oxygen, or (where $R^1$ is —O—$R^8$ and X is carbon) an oxa linkage to X forming a 1,3-dioxolane, wherein the alkyl or alkylidene substituents of $R^1$ can be linked to form a 3 to 7-membered non-aromatic ring, and wherein if X is nitrogen, X is linked to $R^1$ by a single bond and the terminal carbon of $R^1$ that links $R^1$ to N is saturated;

(4) n is 0 or 1, and where if n is 1, $R^{3*}$ is either (C1–C6) alkyl (with the attached nitrogen having a positive charge) or oxygen (forming an N-oxide) and X is carbon;

(5) wherein ring D is a 6-membered ring, a 6-membered ring substituted with a 3 to 6-membered spiro ring, or a 6-membered ring fused with a 5 to 6-membered ring, wherein the fused ring lacking the illustrated tertiary nitrogen can be aromatic, with the proviso that the ring atoms include no quaternary nitrogens:

wherein the carbon and nitrogen ring atoms of ring D can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C1–C6) alkoxy, oxo, hydroxycarbonyl, aryl wherein the aryl is as defined for $R^a$ or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms; and wherein $R^1$, $R^3$ and G are such that at least two atoms separate X and the illustrated ring nitrogen;

(6) wherein ring E is a 6-membered ring, a 6-membered ring substituted with a 3 to 6-membered spiro ring, or a 6-membered ring fused with a 5 to 6-membered ring, wherein the fused ring lacking the illustrated tertiary nitrogen can be aromatic, with the proviso that the ring atoms include no quaternary nitrogens:

wherein the carbon and nitrogen ring atoms of ring E can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C–C6) alkoxy, oxo, hydroxycarbonyl, (C1–C6) alkoxycarbonyl, aryl wherein the aryl is as defined for $R^a$ or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms; and wherein G* and $R^{18}$ are such that at least two atoms separate the illustrated ring nitrogen from the carbon linked to $R^x$ and $R^y$;

(7) $R^{19}$ (a) forms a double bond with $R^1$, $R^3$ or G, (b) is hydrogen (c) is (C1–C3) alkyl or alkylene, or (d) is incorporated into a fused ring;

(8) $R^4$ and $R^{4*}$ are independently hydrogen or (C1–C6) alkyl, or one of $R^4$ and $R^{4*}$ can be (C1–C6) hydroxyalkyl; and (9) R5 is (CO)NR$^{13}$R$^{14}$, (CO)OR$^{15}$, (CO)SR$^{16}$, (SO$_2$)NR$^{17}$R$^{18}$, (PO)(OR$^{19}$)(OR$^{20}$), (CR$^{22}$)(OR$^{23}$)(OR$^{24}$), CN or tetrazol-5-yl, wherein $R^{13}$, $R^{14}$, $R^{15}$, $R^{16}$, $R^{17}$, $R^{18}$, $R^{19}$ and $R^{20}$ are independently hydrogen, (C1–C8) alkyl which can include a (C3–C8) cycloalkyl, wherein the carbon linked to the oxygen of R15 or the sulfur of R16 has no more than secondary branching and, (C2–C6) hydroxyalkyl, aminoalkyl where the alkyl is C2 to C6 and the amino can be substituted with up to two independent (C1–C6) alkyls, arylalkyl wherein the alkyl is C1–C6, heteroarylalkyl wherein the alkyl is C1 to C6, aryl or heteroaryl, $R^{22}$ is hydrogen or $OR^{25}$ and $R^{23}$, $R^{24}$ and $R^{25}$ are (C1–C6) alkyl, phenyl, benzyl, acetyl or, where $R^{22}$ is hydrogen, the alkyls of $R^{23}$ and $R^{24}$ can be combined to include 1,3-dioxylane or 1,3-dioxane:

wherein the aryl is phenyl or naphthyl and the heteroaryl is a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon;

wherein the aryl, heteroaryl, aryl of arylalkyl or the heteroaryl of heteroarylalkyl can be substituted with substituents selected from the group consisting of fluoro, chloro, bromo, nitro, cyano, trifluoromethyl, amidosulfonyl which can have up to two independent (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two independent (C1–C6) alkyl, (C1–C6) alkylsulfonyl amidino that can substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl; and wherein $R^{13}$ and $R^{14}$ together with the nitrogen can form a 5 to 7-membered ring that can contain one additional heteroatom selected from oxygen and sulfur and wherein at least one of $R^{xa}$, $R^{ya}$ and $R^{2a}$ is a heteroaryl comprising diazolyl, triazolyl, tetrazolyl, thiazolyl, isothiazolyl, oxazolyl, isoxazolyl, thiolyl, diazinyl, triazinyl, benzoazolyl, benzodiazolyl, benzothiazolyl, benzoxazolyl, benzoxolyl, benzothiolyl, quinolyl, isoquinolyl, benzodiazinyl, benzotriazinyl, thienyl, furanyl, pyrrolyl, indolyl, isoindoyl or pyrimidyl.

13. The compound of claim 1, wherein $R^1$ is —O—$R^8$ or —S—$R^{8*}$.

14. The compound of claim 1, wherein said second bridge between two of $R^{xa}$, $R^{ya}$ and $R^{2a}$ is L, and satisfies the following formula:

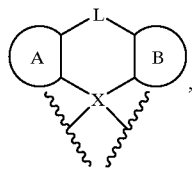

wherein A and B are aryl or heteroaryl groups of $R^{xa}$ and $R^{ya}$, respectively, and wherein L is selected from the group consisting of: (1) (C1–C2) alkyl or alkenyl which can be independently substituted with one or more (C1–C6) alkyl, (2) sulfur, (3) oxygen, (4) amino, which can be substituted for hydrogen with one (C1–C6) alkyl (5) carbonyl, (6) —CH$_2$C(=O)—, which can be substituted for hydrogen with up to two independent (C1–C6) alkyl, (7) —C(=O)—O—, (8) —CH$_2$—O—, which can be substituted for hydrogen with up to two independent (C1–C6) alkyl, (9) —C(=O)—N($R^{24}$)—, wherein $R^{24}$ is hydrogen or (C1–C6) alkyl, (10) —CH$_2$—NH—, which can be substituted for hydrogen with up to three (C1–C6) alkyl, or (11) —CH=N—, which can be substituted for hydrogen with (C1–C6) alkyl, or a single bond whereby two of $R^{xa}$, $R^{ya}$ and $R^{2a}$ are directly linked by the single bond.

15. The compound of claim 14, wherein $R^{xa}$—$R^{xb}$—, $R^{ya}$—$R^{yb}$— and X form:

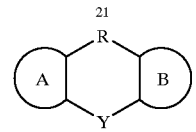

wherein Y is a carbon bonded to $R^1$ by a single or double bond or a nitrogen that is bonded to $R^1$ and wherein $R^{21}$ either (i) completes a single bond linking two aryl or heteroaryl rings of $R^x$ and $R^y$, (ii) is (C1–C2) alkylene or alkenylene, (iii) is sulfur or (iv) is oxygen, and wherein $R^x$ and $R^y$ can be substituted as set forth above.

16. The compound of claim 15, wherein $R^{21}$ is CH$_2$CH$_2$ or CH=CH.

17. The compound of claim 1, wherein the alkylenedioxy substitution of $R^{xa}$, $R^{ya}$ or $R^{2a}$ is as follows:

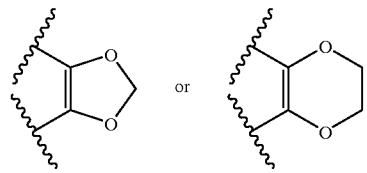

wherein the alkylenedioxy can be substituted with up to two independent (C1–C3) alkyl.

18. The compound of claim 1, wherein ring D is according to one of formulas A' and B':

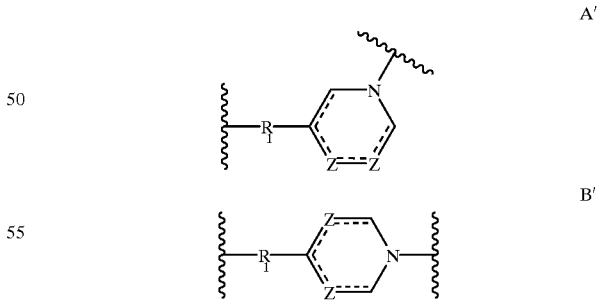

wherein Z represents carbon, wherein for each of formulas A' and B' up to two of the bonds indicated with the hashed lines can be double bonds provided no two double bonds are adjacent, and wherein the ring of formulas A' and B' can be substituted as set forth above for ring D.

19. The compound of claim 1, wherein the ring system comprising G* is according to one of formulas C' and D'

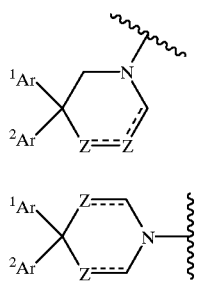

wherein Z represents carbon, wherein for formula C' up to one of the bonds indicated with the hashed lines can be double bond and for formula D' up to two of the bonds indicated with the hashed lines can be double bonds, and wherein the ring can be substituted as set forth above for ring E.

20. The compound of claim 1, wherein ring D or ring E is substituted with up to three substituents.

21. The compound of claim 1, wherein $R^{xa}$ and $R^{ya}$ together can be substituted with up to six substituents, $R^{2a}$, $R^q$, $R^r$ and $R^s$ can each be substituted with up to 3 substituents, and wherein the presence of each of $R^q$, $R^r$ or $R^s$ is considered a substitution to the respective ring structure of $R^{xa}$, $R^{ya}$ and $R^{2a}$.

22. The compound of claim 1, wherein the aryl, heteroaryl, aryl of arylalkyl or the heteroaryl of heteroarylalkyl of $R^{13}$, $R^{14}$, $R^{15}$, $R^{16}$ $R^{17}$, $R^{18}$ $R^{19}$ or $R^{20}$ is substituted with up to three substituents.

23. The compound of claim 1, wherein the compound is an optically pure enantiomer.

24. A pharmaceutical composition comprising an effective amount of a compound of formula I or II, and a pharmaceutically acceptable excipient:

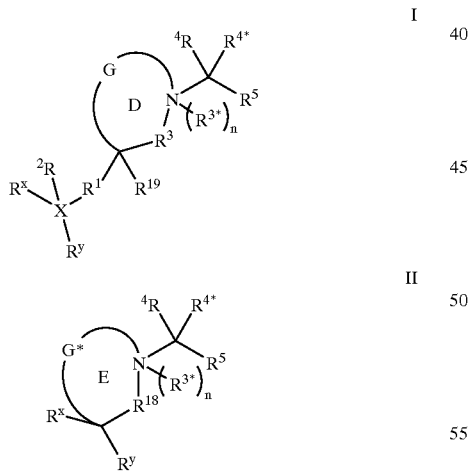

or a pharmaceutically acceptable salt thereof,
wherein:

(1) X is nitrogen or carbon, and $R^2$ is not present when X is nitrogen;

(2) $R^2$ (a) is hydrogen, (C1–C6) alkyl, (C1–C6) alkoxy, cyano, (C2–C7) alkanoyl, aminocarbonyl, (C1–C6) alkylaminocarbonyl or dialkylaminocarbonyl wherein each alkyl is independently C1 to C6, (b) comprises (where $R^1$ is not —O—$R^8$ or —S—$R^{8*}$) hydroxy, fluoro, chloro, bromo or (C2–C7) alkanoyloxy, (c) forms a double bond with an adjacent carbon or nitrogen from one of either $R^1$, $R^{xb}$ or $R^{yb}$, (d) is oxygen forming an oxa linkage with $R^1$ or integrated into ring E (see, for example, Compound C6) or (e) is $R^{2a}$ linked by $R^{2b}$ to X;

($2^i$) $R^x$ is a ring-containing structure $R^{xa}$ linked by $R^{xb}$ to X;

($2^{ii}$) $R^y$ is a ring-containing structure $R^{ya}$ linked by $R^{yb}$ to X;

($2^{iii}$) $R^{xa}$, $R^{ya}$ and $R^{2a}$, are independently aryl, heteroaryl, adamantyl or a 5 to 7-membered non-aromatic ring having from 0 to 2 heteroatoms selected from the group consisting of oxygen, sulfur and nitrogen, wherein:
  (a) aryl is phenyl or naphthyl,
  (b) heteroaryl comprises a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon,
  (c) each of $R^{xa}$, $R^{ya}$ and $R^{2a}$ can be independently substituted with one of $R^q$, $R^rO$— or $R^sS$—, wherein Rq, Rr and Rs are independently aryl, heteroaryl, adamantyl or a 5 to 7-membered non-aromatic ring as these structures are defined for $R^{xa}$, and
  (d) $R^{xa}$, $R^{ya}$, $R^{2a}$, $R^q$, $R^r$ and $R^s$ can be substituted with substituents selected from the group consisting of fluoro, chloro, bromo, nitro, hydroxy, cyano, trifluoromethyl, amidosulfonyl which can have up to two independent (C1–C6) N-alkyl substitutions, adamantyl, (C1–C12) alkyl, (C1–C12) alkenyl, amino, (C1–C6) alkylamino, dialkylamino wherein each alkyl is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two independent (C1–C6) alkyl, (C1–C6) alkylsulfonyl, amidino that can independently substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl, wherein:
    (i) the substitutions of $R^{xa}$, $R^{ya}$ and $R^{2a}$ can be combined to form a second bridge between two of $R^{xa}$, $R^{ya}$ and $R^{2a}$ comprising (1) (C1–C2) alkyl or alkenyl, which can be independently substituted with one or more (C1–C6) alkyl, (2) sulfur, (3) oxygen, (4) amino, which can be substituted for hydrogen with one (C1–C6) alkyl, (5) carbonyl, (6) —CH$_2$C(=O)—, which can be substituted for hydrogen with up to two independent (C1–C6) alkyl, (7) —C(=O)—O—, (8) —CH$_2$—O—, which can be substituted for hydrogen with up to two independent (C1–C6) alkyl, (9) —C(=O)—N($R^{24}$)—, wherein $R^{24}$ is hydrogen or (C1–C6) alkyl, (10) —CH$_2$—NH—, which can be substituted for hydrogen with up to three (C1–C6) alkyl, or (11) —CH=N—, which can be substituted for hydrogen with (C1–C6) alkyl, or wherein two of $R^{xa}$, $R^{ya}$ and $R^{2a}$ can be directly linked by a single bond;

($2^{iv}$) $R^{xb}$ and $R^{2b}$ are independently a single bond or (C1–C2) alkylene;

(2') $R^{yb}$ is a single bond, oxa, (C1–C2) alkylene, ethenylene or —CH= (where the double bond is with X), thia, methyleneoxy or methylenethio, or either —N($R^6$)— or —CH$_2$—N($R^{6*}$)—, wherein $R^6$ and $R^{6*}$ are hydrogen or (C1–C6) alkyl, wherein when X is nitrogen X is not bonded to another heteroatom;

(3) $R^1$ comprises: a single bond or double bond; a straight-chained (C1–C3) aliphatic group; or (where X is carbon and $R^{yb}$ does not include a heteroatom attached to X) —O—$R^8$ or —S—$R^{8*}$, wherein either $R^8$ or $R^{8*}$ is a single bond, (C1–C3) alkylene or (C2–C3) alkenylene and O or S is bonded to X:

wherein $R^1$ can be substituted with up to one hydroxy, up to one (C1–C6) alkoxy or up to one (C2–C7) alkanoyloxy, with up to two independent (C1–C6) alkyl, with up to one oxo, up to one (C1–C6) alkylidene, with the proviso that the hydroxy, alkoxy, alkanoyloxy, oxo substituents are not bonded to a carbon that is bonded to a nitrogen or oxygen, or (where $R^1$ is —O—$R^8$ and X is carbon) an oxa linkage to X forming a 1,3-dioxolane, wherein the alkyl or alkylidene substituents of $R^1$ can be linked to form a 3 to 7-membered non-aromatic ring, and wherein if X is nitrogen, X is linked to $R^1$ by a single bond and the terminal carbon of $R^1$ that links $R^1$ to N is saturated;

(4) n is 0 or 1, and where if n is 1, $R^{3*}$ is either (C1–C6) alkyl (with the attached nitrogen having a positive charge) or oxygen (forming an N-oxide) and X is carbon;

(5) wherein ring D is a 6-membered ring, a 6-membered ring substituted with a 3 to 6-membered spiro ring, or a 6-membered ring fused with a 5 to 6-membered ring, wherein the fused ring lacking the illustrated tertiary nitrogen can be aromatic, with the proviso that the ring atoms include no quaternary nitrogens:

wherein the carbon and nitrogen ring atoms of ring D can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C1–C6) alkoxy, oxo, hydroxycarbonyl, aryl wherein the aryl is as defined for $R^a$ or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms; and wherein $R^1$, $R^3$ and G are such that at least two atoms separate X and the illustrated ring nitrogen;

(6) wherein ring E is a 6-membered ring, a 6-membered ring substituted with a 3 to 6-membered spiro ring, or a 6-membered ring fused with a 5 to 6-membered ring, wherein the fused ring lacking the illustrated tertiary nitrogen can be aromatic, with the proviso that the ring atoms include no quaternary nitrogens:

wherein the carbon and nitrogen ring atoms of ring E can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C–C6) alkoxy, oxo, hydroxycarbonyl, (C1–C6) alkoxycarbonyl, aryl wherein the aryl is as defined for $R^a$ or heteroaryl wherein the heteroaryl is as defined for $R^a$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms; and wherein G* and $R^{18}$ are such that at least two atoms separate the illustrated ring nitrogen from the carbon linked to $R^x$ and $R^y$;

(7) $R^{19}$ (a) forms a double bond with $R^1$, $R^3$ or G, (b) is hydrogen (c) is (C1–C3) alkyl or alkylene, or (d) is incorporated into a fused ring;

(8) $R^4$ and $R^{4*}$ are independently hydrogen or (C1–C6) alkyl, or one of $R^4$ and $R^{4*}$ can be (C1–C6) hydroxyalkyl; and (9) R5 is (CO)NR$^{13}$R$^{14}$, (CO)OR$^{15}$, (CO)SR$^{16}$, (SO$_2$)NR$^{17}$R$^{18}$, (PO)(OR$^{19}$)(OR$^{20}$), (CR$^{22}$)(OR$^{23}$)(OR$^{24}$), CN or tetrazol-5-yl, wherein $R^{13}$, $R^{14}$, $R^{15}$, $R^{16}$, $R^{17}$, $R^{18}$, $R^{19}$ and $R^{20}$ are independently hydrogen, (C1–C8) alkyl which can include a (C3–C8) cycloalkyl, wherein the carbon linked to the oxygen of R15 or the sulfur of R16 has no more than secondary branching and, (C2–C6) hydroxyalkyl, aminoalkyl where the alkyl is C2 to C6 and the amino can be substituted with up to two independent (C1–C6) alkyls, arylalkyl wherein the alkyl is C1–C6, heteroarylalkyl wherein the alkyl is C1 to C6, aryl or heteroaryl, $R^{22}$ is hydrogen or OR$^{25}$ and $R^{23}$, $R^{24}$ and $R^{25}$ are (C1–C6) alkyl, phenyl, benzyl, acetyl or, where $R^{22}$ is hydrogen, the alkyls of $R^{23}$ and $R^{24}$ can be combined to include 1,3-dioxylane or 1,3-dioxane:

wherein the aryl is phenyl or naphthyl and the heteroaryl is a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon;

wherein the aryl, heteroaryl, aryl of arylalkyl or the heteroaryl of heteroarylalkyl can be substituted with substituents selected from the group consisting of fluoro, chloro, bromo, nitro, cyano, trifluoromethyl, amidosulfonyl which can have up to two independent (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two independent (C1–C6) alkyl, (C1–C6) alkylsulfonyl, amidino that can substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl; and wherein $R^{13}$ and $R^{14}$ together with the nitrogen can form a 5 to 7-membered ring that can contain one additional heteroatom selected from oxygen and sulfur.

25. A compound of claim 1 according to the following formula

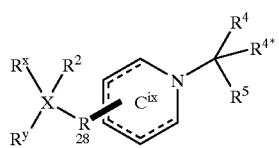

wherein $R^{28}$ is the same as $R^1$ except that the bond to the ring is not a double bond, wherein ring $C^{ix}$ is mono or di-unsaturated at one or more of the bonds indicated with the dashed lines with the double bonds formed between ring carbons and no two double bonds are adjacent, wherein ring $C^{ix}$ can include a fused phenyl and can be substituted as follows the carbon and nitrogen ring atoms of ring D can be substituted with up to 2 substituents selected from (C1–C6) alkyl, (C2–C6) alkenylene, cyano, nitro, trifluoromethyl, and (C2–C7) alkyloxycarbonyl.

* * * * *